United States Patent [19]
Gronningsaeter et al.

[11] Patent Number: 6,019,724
[45] Date of Patent: Feb. 1, 2000

[54] METHOD FOR ULTRASOUND GUIDANCE DURING CLINICAL PROCEDURES

[76] Inventors: Aage Gronningsaeter, Kroppanmarka 112, N-7039 Trondheim; Bjorn Olstad, OSv. 39D, N-7053 Trondheim; Geirmund Unsgaard, N-7510, Skatval, all of Norway

[21] Appl. No.: 08/894,229

[22] PCT Filed: Feb. 8, 1996

[86] PCT No.: PCT/NO96/00029

§ 371 Date: Oct. 28, 1997

§ 102(e) Date: Oct. 28, 1997

[87] PCT Pub. No.: WO96/25881

PCT Pub. Date: Aug. 29, 1996

[51] Int. Cl.[7] ................................................. A61B 8/00
[52] U.S. Cl. .......................................................... 600/439
[58] Field of Search ........................... 600/437, 439, 600/443, 414, 417, 424, 426, 427, 429, 461; 128/916; 606/130

[56] References Cited

U.S. PATENT DOCUMENTS

| | | | |
|---|---|---|---|
| 5,078,140 | 1/1992 | Kwoh | 606/130 |
| 5,411,026 | 5/1995 | Carol | 600/439 |
| 5,447,154 | 9/1995 | Cinquin et al. | 601/2 |
| 5,483,961 | 1/1996 | Kelly et al. | 606/130 |
| 5,503,152 | 4/1996 | Oakley et al. | 128/916 |
| 5,531,227 | 7/1996 | Schneider | 606/130 |
| 5,558,091 | 9/1996 | Acker et al. | 128/899 |
| 5,647,373 | 7/1997 | Paltieli | 600/461 |
| 5,851,183 | 12/1998 | Bodiolz | 600/443 |

*Primary Examiner*—Francis J. Jaworski
*Attorney, Agent, or Firm*—Dennison, Meserole, Scheiner & Schultz

[57] ABSTRACT

A method for generating quasi-realtime feedback for the purpose of guiding surgical, therapeutic or diagnostic procedures by means of ultrasound imaging, wherein the location of a surgical tool, therapeutic radiation field or a diagnostic energy field is related to the coordinate system of an intraoperative 2D and/or 3D ultrasound imaging system and, optionally, to pre-operative MR/CT/X-ray data, thus allowing synchronized relations between data acquisition, tool movement and image visualizations.

18 Claims, 18 Drawing Sheets

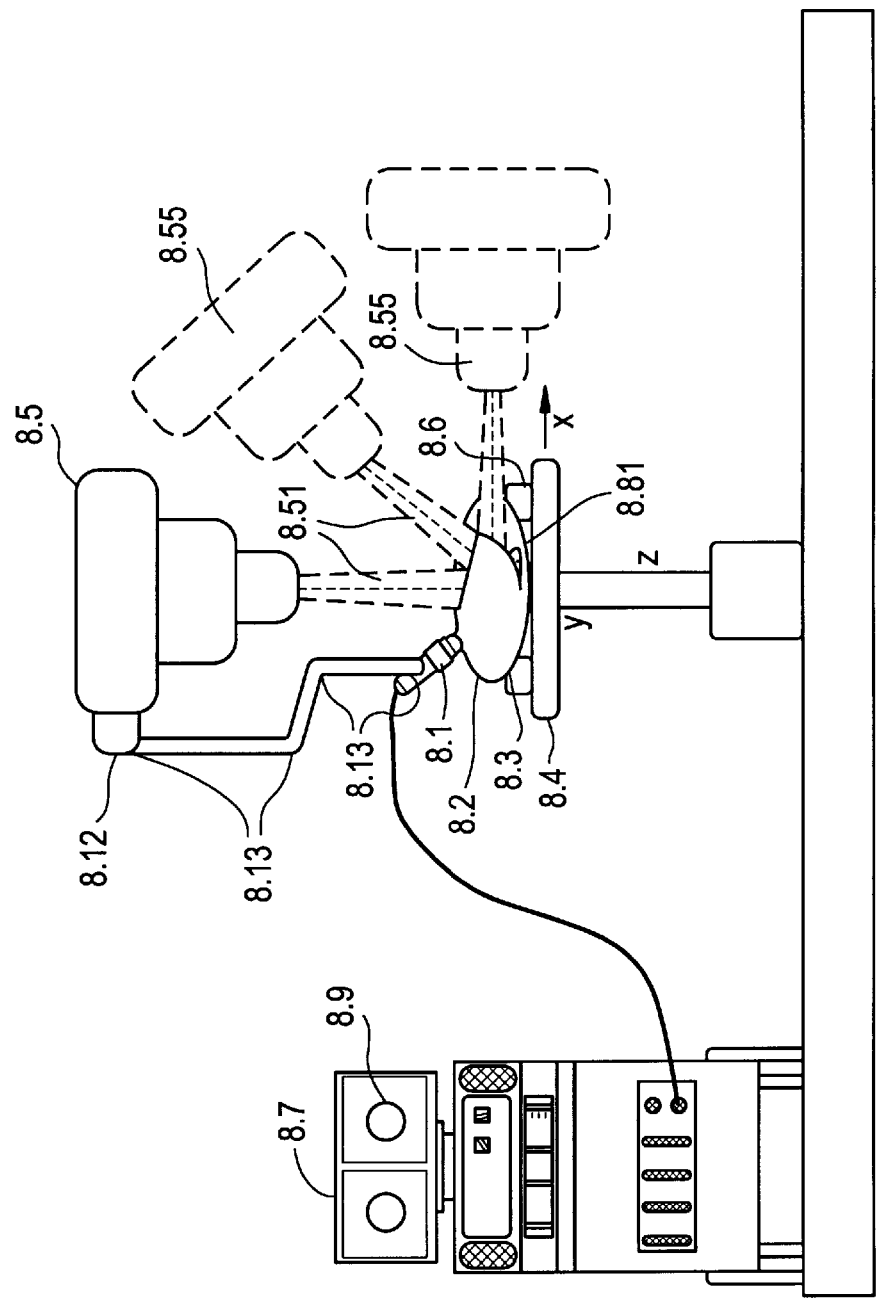

METHOD FOR ULTRASOUND GUIDANCE DURING CLINICAL PROCEDURES

This application is a 371 of PCT/N096/00029 filed Feb. 8, 1996.

BACKGROUND OF THE INVENTION

This invention relates to a method for generating useful real-time feedback about tissue characteristics and the position of anatomical objects relative to at least one tool used during clinical procedures in living biological structures, employing an ultrasonic transducer/probe.

Thus, more specifically, the invention relates to the field of ultrasound imaging during a clinical procedure that involves a tool being inserted into the imaged scene, particular methods for combining the geometric localization of the said tools relative to the acquired ultrasound images.

The method to be described here comprises a combination of acquisition of ultrasonic images, localization of tools and/or tool trajectories used during the clinical procedure, processing of the ultrasonic images based on the knowledge of the position of the tools in the imaged scene in order to obtain visualizations with real-time feedback to the operator. The visualizations integrate information obtained both from the ultrasonic images and the geometric localizations of the tools in the imaged scene. The invention describes alternative procedures for obtaining the geometric localization of tools and describes how the said images and geometric localization's can be processed in order to obtain useful feedback based on the information content in both data sources (ultrasonic images and tool positions).

The method finds application in surgical, therapeutic and diagnostic procedures.

The term clinical procedure will be used throughout this invention to designate:

1. Any invasive diagnostic, therapeutic or surgical procedure as for example: open surgery, endoscopic/laparascopic surgery, cyst aspiration, biopsy (sampling), injection, implantation etc.

2. Any therapeutic and/or diagnostic procedure based on energy emission in terms of fields, waves or particles, for example: radiotherapy, laser therapy or ultrasound therapy (ultrasound hyperthermia or shockwaves)

3. Any similar clinical procedure where at least one mechanical object and/or energy field is applied to the imaged, living biological structures.

The term tool will be used throughout this invention to designate:

1. A surgical tool used in a clinical procedure, for example: a cutting or resecting device (scalpel, diathermy, scissors, suction, ultrasound aspirator, thermal knife, laser, argon beam), a coagulating device (monopolar or bipolar diathermy, laser), a stapler, biopsy forceps, needle, cannula etc.

2. An imaging device like an ultrasound catheter, ultrasound probe or any optical imaging system.

3. Combined devices such as an endoscope that includes imaging capabilities and at least one surgical tool as described above.

4. An external beam or energy field applied in for example: radiotherapy, laser therapy or ultrasound therapy.

5. Any similar devices or fields that can be coregistered with the acquired ultrasonic images.

The term quasi real-time will be used throughout this invention to designate that a process (like ultrasound data acquisition, position determination of tools in the imaged scene and/or data visualization) runs fast enough to allow for interactive feedback/operation by the user. This includes truely real-time where the absolute time delay between data acquisition and the final data visualization is below the acceptable level for interactive feedback. In addition, we will use the term quasi real-time to refer to processes that appear as truely real-time to the user.

This can for example be accomplished by a repetitive 3D ultrasound acquisition where the repitition rate exceeds the criteria for interactive operation, but where the position determination and data visualization are performed in real-time based on the latest available 3D data set.

The term positioning system will be used throughout this invention to designate:

1. Any system that provide information about the position and/or direction of an ultrasound probe, a tool or other objects within the operating theater. The positioning system can optionally provide mechanical support by limiting the movement of the ultrasound probe, tool or other objects to a predetermined space, plane, direction or point.

2. The positions and/or directions are determined by measurements or by predetermined geometry.

3. Position measurement is achieved by any magnetic, electromagnetic, optical or acoustical system (wireless or not) or by any mechanical arrangement with angle and/or position sensors.

Technology development has accelerated the use of non-invasive and minimally invasive techniques in medicine. The use of energy fields, waves, needles, catheters and endoscopic instruments allow diagnosis, treatment and surgical procedures in most parts of the human body. The patient trauma is reduced, the cost and the hospitality time is reduced, and procedures can be performed that was not possible before.

Such techniques require positioning and manipulation of tools in relation to organs and other biological structures within the body, all which may be hidden for visual inspection of the human eye. The irregular and unpredictable shape and position of most biological structures and organs makes absolute positioning within the body difficult or impossible from the outside. Positions and shapes may also change during the procedure. Various imaging techniques are currently in use to provide geometric information to the operator, prior to, during and after the procedure.

Preoperative MR, CT or X-ray scans are commonly used in order to utilize a description of a lesion and its relation to other structures. Allthough MR and CT systems provide 3D data, these techniques suffer from some drawbacks: i) The instruments are huge, non-portable and the investments costs are high. ii) Interactive imaging and surgery is normally not possible. iii) Biological structures that move or deformate during the clinical procedure or between diagnostic imaging and the clinical procedure, limits the value of such imaging techniques. iv) CT and X-ray systems expose the patient to ionizing radiation which may damage tissue and cause cancer.

Endoscopic techniques based on optics or a video camera provide high quality and real-time visualizations which allows intra-operative procedures. However, the lack of penetration through biological structures limit their use.

The ultrasound technology has several advantages in that it penetrates through biological structures, the instruments are portable, and interactive imaging during the procedure is possible, even in real time. This means that structures that change during the clinical procedure can be monitored continously or repetitively. There are large potentials in integrating the use of ultrasound imaging and Doppler techniques in clinical procedures for the purpose of monitoring and guidance.

SUMMARY OF THE INVENTION

On the background of known techniques this invention takes as a starting-point known methods for acquisition of 2D and 3D ultrasonic images and established clinical procedures where at least one tool is applied to the imaged, living biological structures. The invention describes new techniques for computation of 2-dimensional and 3-dimensional ultrasonic images and/or visualizations that utilizes the localization of at least one tool in the imaged scene. The methods to be described allow extension of non-invasive and minimally invasive techniques by providing valuable additional features to existing technology.

The use of imaging modalities for guiding clinical procedures is established techniques, and both previously acquired images and intraoperative real-time imaging are performed.

i) Previously acquired images: The value of previously acquired images is limited to cases where the anatomical structures do not change very much. Brain surgery is an example of one area where this technique is widely used and where new technology develops rapidly. Previously acquired MR/CT and angiograms form the basis for planning the location of the craniotomy and the least damaging route down to the lesion. The access to multiplane images provide information about the size and location of a lesion relative to other structures, and this information helps the surgeon to perform for example free-hand catheter/needle interventions into a lesion. However, the accuracy is limited. Stereotaxy has been developed in order to improve the accuracy in navigating tools within the brain [1], but this mechanical system is cumbersome to use, and it provides no other information than the position and direction of a tool relative to the coordinate system of the previously acquired images.

Lately, image guided surgery techniques has been developed which consist of a system for measuring the position and direction of a surgical tool relative to previously acquired digital 3D images. With this technique, the surgeon can move the tool freely by hand and simultaneously observe on a monitor, a set of images or other visualizations, which in some way are related to the position and/or direction of the tool. Such a system is described by Galloway et al. where the position of the tool was measured by a six-degree-of-freedom articulated arm [2]. A commercial product based on the same method is the "The Viewing Wand" which was developed by ISG Technologies Inc. (Ontario, Calif.).

A challenge in image guided surgery techniques is to relate the coordinate system of the previously acquired images to the coordinate system of the tool positioning system. This problem is solved by calibration in the Viewing Wand system: the tip of the tool is located on some points on the patient head whose coordinates are known to the image data base.

Such systems have advantages over for example stereotaxy in that it is less cumbersome, the tool can be moved freely, and image information is available prior to and during intervention. The route down to the lesion can be planned and the actual intervention can be monitored to the extent one can trust the accuracy of the coordinate system alignment. However, the method has limited or no value in situations where the biological structures changes during the procedure, for example during resection of tumors that shrink during surgery or during aspiration of cysts or ventricles.

ii) Intraoperative real-time imaging: Ultrasound imaging is currently used to guide different kind of surgical procedures. Several authors have demonstrated the value of using ultrasound imaging to determine the shape and location of a lesion in the brain in order to plan the least damaging route down to it. However, the accuracy in hitting a deep-sited cyst or tumor with a needle from the brain surface is very low and the success rate depends on the operators skills [3, 4].

A tool that improves the accuracy and success-rate is a mechanical device that is fixed to the ultrasound probe. It contains a guiding channel for a needle whose direction coincide with the ultrasound scan plane. The angle can be tilted and the direction of the needle is marked and superimposed on the ultrasound image. The drawback with this method is that needle intervention is performed under real-time 2D imaging guidance only (in contrast to real-time 3D) and the flexibility in manipulating the needle is low.

What is novel and specific in the method according to the invention is summarized in the following (this will be defined more specifically in the appended claims):

1. A clinical procedure is guided interactively by quasi real-time ultrasonography. More specifically, the planning and/or execution of a surgical, therapeutic or diagnostic procedure is guided by on-site ultrasound imaging which allows interactive tool manipulation with arbitrary positioning of the tool(s) relative to the imaging device including freehand movement of the tool or the imaging device. The procedure is guided by quasi real-time feedback through ultrasonographic visualizations. The method can optionally include preciously acquired images and provide visualizations that combine on-site ultrasound images with the preoperative scans.

2. The main advantage of this method is the on site and quasi real-time imaging capability which extents its use to applications where the shape and/or location of organs and other biological structures change during the procedure. One examples is removal of brain tumors where surrounding tissue collapse during resection. Another example is the problem of positioning a tumor or other lesion in the dose-planning and in the radio-therapy machines. Dose planning and therapeutic radiation is performed in different equipment and typically with several days time interval. Organs in the abdomen is especially subject to movements between dose planning and therapeutic radiation.

3. The position of a surgical tool can be registered directly in the ultrasound image in situations where the tool is located in the image field. The tool position relative to the ultrasound image coordinates as well as relative to other biological structures can be measured directly. The process of relating an image coordinate set to a tool position coordinate system is obsolete. No calibration procedure is required thus eliminating the risk of misalignments between the coordinate systems. Misalignments during the procedure can be difficult to discover, especially if the calibration is performed once and prior to the surgery.

4. The invention describes the possibility of letting the tool include a second ultrasound probe. This allows calculation of combined visualizations as for example "bifocal imaging": The image from a high resolution (low penetration) imaging device (located at the tip of tool) may for example be superimposed on in the image from a lower resolution overview scanner.

5. Combined use of ultrasound imaging and one or more previously acquired image data bases have several advantages. One can correlate an in on-site ultrasound 3D image with a 3D data set from a previously acquired image data base and make these coordinate sets coincide with each other as well as coincide with the tool position coordinate system. The accuracy and confidence in the positioning is increased. Furthermore, the use of previously acquired images (with high image quality) can be extended to cases with tissue movement. The ultrasound imaging system can track the movement of an organ or other biological structures and transfer the change in coordinate systems to the previously acquired data base.

BRIEF DESCRIPTION OF THE DRAWINGS

The invention shall be explained more closely in the following description of various embodiments with reference to the drawings, in which:

FIGS. 8(a) and 9 illustrate simplified versions of FIGS. 7 (a) and (b) where the ultrasound probe movement is limited so that the ultrasound scan plane intersects the center of radiation. This reduces investment costs at the expense of freedom of operability.

DESCRIPTION OF THE PREFERRED EMBODIMENTS

This invention is applicable in surgery, therapy and diagnosis, and possible clinical fields include abdominal, urological, toraxial, gastroenterological, neurosurgical, gyneocological and orthopedical applications. The invention is described through specific examples of how the method can be applied, a summary at the end of this section and the appended claims and illustrations.

Several examples are provided from three different clinical cases: I) Deep sited brain intervention, II) Open and endoscopic brain tumor resection and III) Radiotherapy.

Case I. Deep Sited Brain Intervention

The method described in this case is minimal invasive brain interventional procedure such as biopsy, aspiration or equivalent at a deep sited location in the brain, guided by ultrasound. A tool is inserted into the lesion through the normal parenchyma by ultrasound imaging guidance in order to find the least damaging route to the site. The tool can either be inserted through the burr-hole or craniotomy that is made for the ultrasound probe. However, it may be more convenient to drill an extra hole for the tool in order to obtain a different angle of incident. There is a need for localizing the tool in relation to biological structures, information that can be achieved by several methods, including:

i) Determine the tool position by measuring the absolute position of the tool in a fixed coordinate system and integrate anatomical information provided by an imaging technique into the same coordinate system. This method is described in detail in Example 1.

ii) Determine the tool position by measuring the tool position relative to the coordinate system of the ultrasound image. A detailed description is provided in Example 2.

iii) Determine the tool position relative to biological structures by direct visualization in an ultrasound image as described in Example 3.

Example 1

Description

Figure 1:
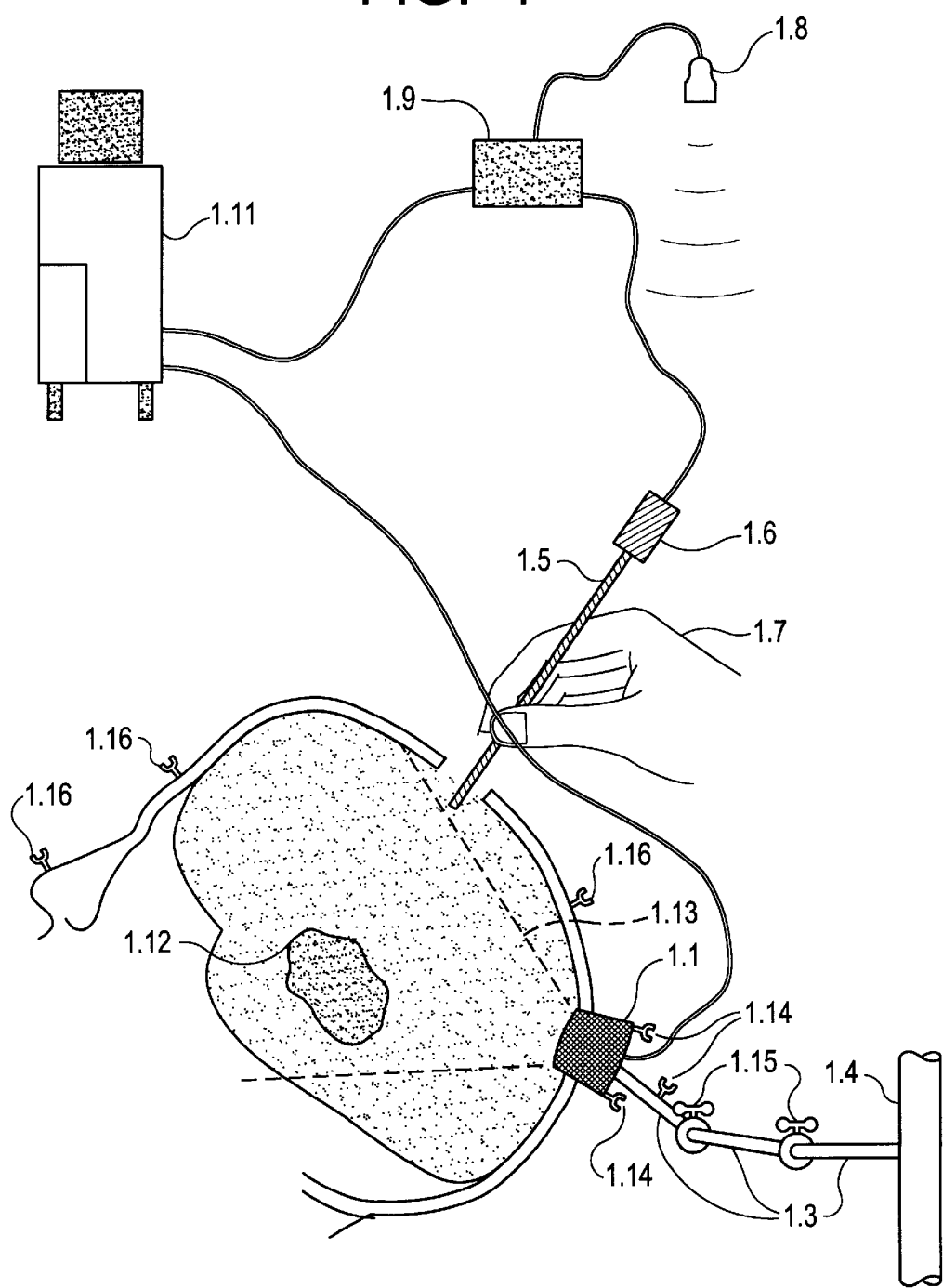
FIG. 1 illustrates a system for ultrasound guided intervention (biopsy, aspiration or equivalent) in the brain. An ultrasound probe is located on the brain surface in a burrhole or craniotomy. A surgical tool in inserted through the same or a different hole in the skull. The positions of the probe and the tool are measured and coregistered in the computer.

The system illustrated in FIG. 1 consists of an ultrasound instrument 1.11 with a built in computer 1.10 that communicates with the ultrasound instrument. A 3D positioning system that is based on low frequency magnetic fields is connected to the computer. The positioning system consists of a control unit 1.9, a source 1.8 and a sensor 1.6. One possible realization of 1.6, 1.8 and 1.9 is the product 3SPACE ISOTRAK (Polhemus Navigation Science, Colchester, Vt.) which is based on low frequency magnetic fields. The sensor is connected by cable to a tool 1.5 which can be moved freely by hand 1.7. The position and direction of the sensor 1.6 is measured several times per second, and the position and direction of the tool can thereby be calculated relative to the source 1.8. An alternative system is the OPTOTRACK (Northern Digital Inc., Ontario, Canada).

An ultrasound probe 1.1 is connected to the ultrasound instrument by a cable and the probe is mounted to a fixed point 1.4 like for example the bed by a positioning system which consists of three stiff arms 1.3 that are interconnected by flexible ball joints with locks 1.15. The flexible ball joints 1.15 are unlocked and the ultrasound probe is located on the brain surface 1.2 aligned until a good ultrasound image of the lesion and surrounding tissues is provided. The flexible ball joints 1.15 are unlocked in order to fix the ultrasound probe in the same position throughout the procedure. Initial calibration is required in order to relate the coordinate system of the ultrasound probe 1.1 to the coordinate system of the source 1.8. This is achieved by touching the tip of the tool on three landmarks 1.14 located on the ultrasound probe 1.1 and its arm. The ultrasound probe provide 3D information about the size and shape of the lesion as well as its relation to other biological structures.

Preoperative MR of CT images is loaded into the computer prior to the procedure, and a calibration of the topographic coordinate system relative to the magnetic positioning system is performed by measuring the position of the landmarks 1.16 (located on the patients head during preoperative scan) by touching them with the tip of the tool.

Use

The computer calculates repeatedly the position of the tool tip and the direction of the tool. The surgeon can now plan the least damaging route to the lesion by aiming the tool towards the lesion and by observing a set of images that is displayed with an update rate of several images per second.

Image selection is done by the computer according to a pre defined format and based on the tool direction. One example is to display two perpendicular planes of ultrasound and MR/CT data that intersect along the aiming trajectory. The surgeon can plan the route in advance and if desirable, mark some milestones that can be used during tool insertion to give an alarm if the actual trajectory deviates too much from the planned route.

The tool intersection is done by free hand which means that minor tilting and pushing is acceptable during the procedure. During intersection, there are two different options for visualization: i) The image selection is given by the tool direction, the scenes change by tool manipulation. ii) The image selection is specified in advance and stay constant during the procedure (or during parts of it). The imaging scenes include the lesion, and the tool direction is superimposed as lines or symbols on the MR/CT/ultrasound images. As the tool enter into the quasi real-time ultrasound image, it is visualized directly.

Visualizations/graphic presentations are computed that utilize the relative position between the scene imaged by the ultrasound transducer and the tools inserted in the imaged scene. 10.1, 10.2, 10.3 and 10.4 illustrate 2D ultrasonic images either obtained with 2D imaging or by extraction of a 2D image from a 3D ultrasonic image. The known localization of a tool is superimposed on the 2D images (10.5). Similarly, the tool (10.6) and the tool trajectory (10.7) can be superimposed on a 2D image. If the tool is not inside the plane defined by the 2D ultrasonic image, then the tool or tool trajectory will intercept the 2D image in a single point (10.8). In this case one can also provide feedback on the distance between the 2D image and the tip of the tool if only the tool trajectory intercepts the 2D image. Similarly, one can provide feedback to the user about the relative orientation between the tool and the 2D image. 10.9 illustrates a tool given by for example a radiation field that has a 2 dimensional interception with the 2D image.

The tools or tool trajectories can also be added to visualizations of 3 dimensional ultrasound data. 11.1 illustrates a 3D ultrasonic dataset where the tool (11.5) and the tool trajectory (11.6) are superimposed on the rendering. A visualization created by slicing through the 3D dataset is illustrated by 11.2 where a cavity 11.7 is shown together with the tool 11.8 and the tool trajectory 11.9. These visualizations can be combined with 2D images extracted from the 3D dataset 11.3 and 11.4 where the tools are indicated (11.10,11.11) as described earlier in the invention.

Tools inserted in the scene imaged by the ultrasound transducer might produce an acoustical shadow behind the tool. 12.1 illustrates a 3D dataset where a tool 12.3 produces the shadow 12.4. Similarly, in the 2D image 12.2 with the tool 12.5 and the tool trajectory 12.6 the shadow 12.7 is produced.

Knowing the position of the tool one can compute which regions in the 2D or 3D imaged where the ultrasound beam has been affected by the tool. Knowledge about the beam profile and the point spread function further increase the possibility to accurately locate the image samples in a 2D or 3D ultrasonic image that have been affected by the tool. These artifacts can either be corrected by inserting measurements from earlier 2D or 3D images when the tool was in a different position or simply by making the affected measurements transparent in a visualization of a 3 dimensional scene. In a 3 dimensional visualization the affected spatial locations can be made transparent such that the image artifacts are not included in the derived visualizations.

Visualization of soft 3D tissues based on ultrasonic imaging is in general very difficult. During a clinical procedure the operator is usually particularly interested in the geometry in the vicinity of the tip of the tool. This fact can be actively exploited by assigning an opacity field which is computed relative to the position of the inserted tool. 13.1 illustrates a 3D ultrasonic dataset with a tool 13.3 and the tool trajectory 13.4. An opacity field 13.5 is indicated as a rotationally symmetric region around the tool trajectory. Any shape for the opacity field might be applied, but the field is moved through the 3D scene according to the movements of the tool inside the imaged scene. 13.2 illustrates a 3D visualization with a cavity 13.9 as an example. The tool 13.7, tool trajectory 13.8 and the associated opacity field 13.6 are illustrated. In other examples like radio therapy the opacity field can be specified as the set of volume elements that will be exposed to the radiation field. This setting is illustrated with a 3D ultrasonic dataset 13.10 and the associated radiation field/opacity field 13.11.

The described opacity field can also be utilized to optimize the acquisition of a 3D ultrasonic dataset. The spatial resolution can be optimized inside the high-opacity regions and the resolution outside this region can either be lower or completely ignored. As a special case, the opacity field can constitute an arbitrarily positioned 2D plane and the 3D acquisition can also in this case be optimized in order to acquire a minimal amount of data with a maximal resolution around the 2D plane.

The position of the tool can be utilized to extract 2D planes from an ultrasonic 3D data set. 14.1 illustrates a 3D dataset. A tool 14.2 and the tool trajectory 14.3 are also indicated. In this example a 2D plane is extracted relative to the tool position such that the tool/tool trajectory is a normal vector to the extracted plane and such that the distance between the extracted plane and the tip of the tool can be controlled by a user parameter. 14.5 illustrates the 2D plane visualized together with a marker 14.6 indicating the intersection with the tool or tool trajectory. The content of 14.5 will hence change according to the movement of the tool 14.2. Similarly, other relative orientations of the 2D plane relative to the tool position can be specified. Of particular interest are 2D planes that intercept the tool along a line and not a single point. The tool position can also be utilized to control the viewing parameters of visualizations computed from a 3D dataset. 14.7 illustrates a 3D visualization with a cavity 14.8 as an example. The visualization can be created by slicing the 3D dataset with a 2D plane and creating the visualization by raytracing along lines that start in the 2D plane and are perpendicular to the 2D plane. Similar or equivalent volume rendering techniques might also be applied. The viewing direction is hence given by the location of the 2D plane slicing the 3D dataset. The localization of this plane cam hence be controlled by the same techniques that we have given for extraction of 2D planes relative to the tool position. 14.9 and 14.10 illustrate a tool and the tool trajectory respectively. In this case the tool is contained inside the 2D plane used to define the viewing orientation of the 3D visualization. Similarly, 14.4/14.5 could have been used as the 2D slice plane such that the 3D visualization is computed along rays parallel with the orientation of the tool.

The tool might include an imaging device like high resolution ultrasound or video imaging. 15.1 illustrates a 3D ultrasonic dataset. 15.2 and 15.3 indicate a tool and the tool trajectory respectively. An example with a high resolution ultrasound image (15.4) acquired from the tip of the tool is indicated. The high resolution 2D image can be displayed separately (15.5), but also integrated into the rendering of the 3D scene (15.1/15.4). Another example of such integration is given by 15.5 which illustrates a 3D visualization with a cavity (15.7) as an example. A tool 15.8 and the tool trajectory 15.9 are indicated. The high resolution 2D ultrasound image (15.10) is integrated in a coregistered manner to the 3D visualization.

Figure 16A:
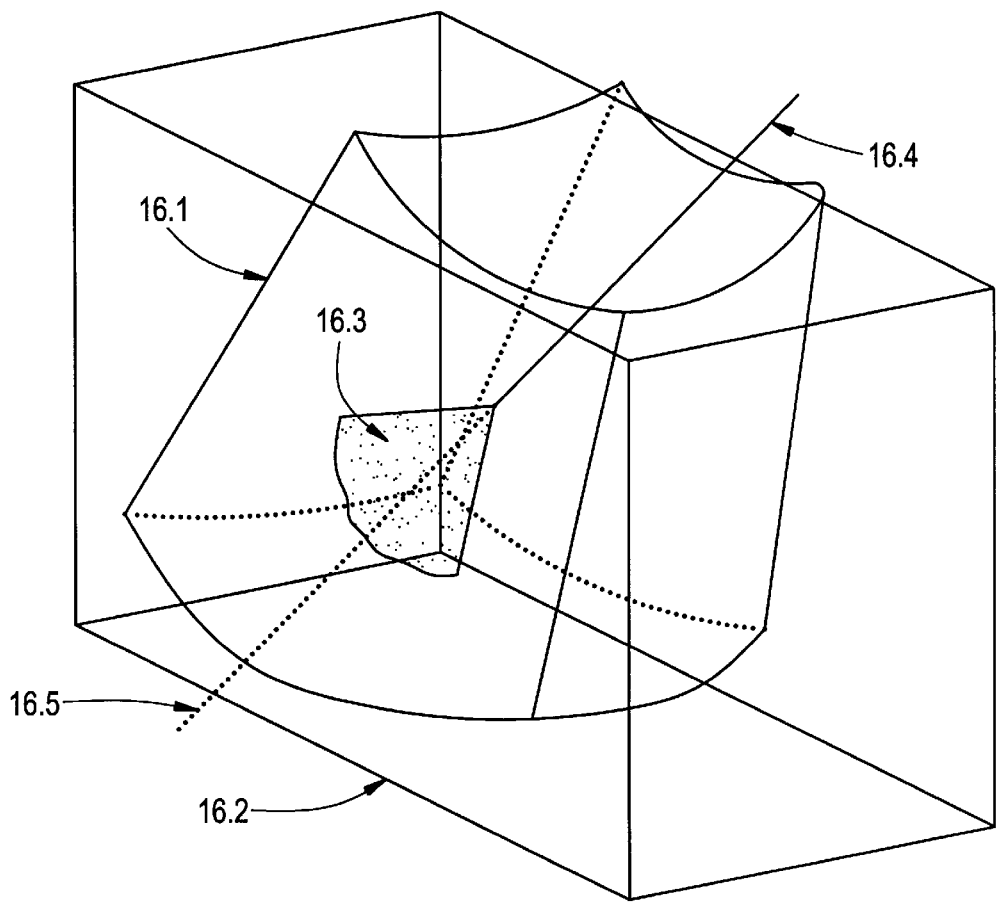
FIG. 16 illustrates how a secondary 2D/3D image (including all pre-operative and/or intra-operative medical imaging modalities such as: a high resolution ultrasonic 2D/3D image, a magnetic resonance 2D/3D image, a computer tomographic 2D/3D image, a X-ray image, an arteriogram and/or a video image is related to the ultrasound acquisitions described elsewhere in the invention. All techniques described in this invention on 2D and 3D visualizations/presentations of ultrasonic data and/or tool positions can therefore be extended with mixed or additional visualizations where the image data is fetched in the secondary 2D/3D image in stead of the ultrasonic imaging device used on site during the clinical procedure.
Figure 16B:
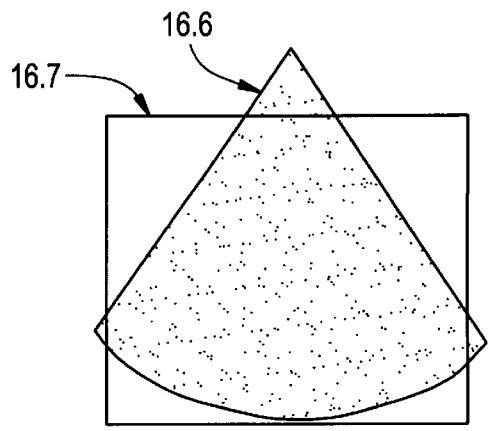
Figure 16C:
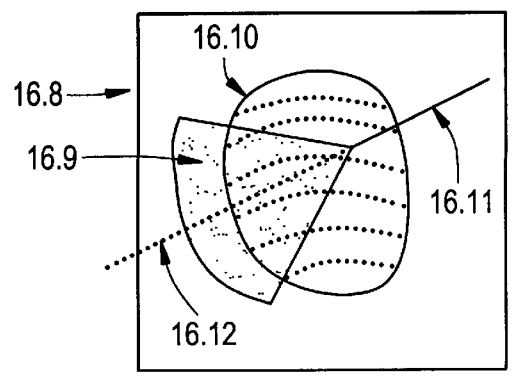

FIG. 16 illustrates how a secondary 2D/3D image 16.2 (including all pre-operative and/or intra-operative medical imaging modalities such as: a high resolution ultrasonic 2D/3D image, a magnetic resonance 2D/3D image, a computer tomographic 2D/3D image, a X-ray image, an arteriogram and/or a video image) is related to the ultrasound acquisitions described elsewhere in the invention (16.1). All techniques described in this invention on 2D and 3D visualizations/presentations of ultrasonic data and/or tool positions can therefore be extended with mixed or additional visualizations where the image data is fetched in the secondary 2D/3D image in stead of the ultrasonic imaging device used on site during the clinical procedure. The figure contains two examples of visualizations that can be combined with coregistered image data from the secondary image (16.2). 16.6 illustrates a 2D ultrasound image acquired on site and a coregistered image 11.7 extracted from the secondary image 16.2. 16.8 illustrates a 3D visualization as described earlier in the invention with a cavity 16.10. The tool 16.11, tool trajectory 16.12 and a high resolution ultrasound image 16.9 are indicated. The visualization can be mixed with either 2D images or 3D visualizations based on the secondary image 16.2. Both visualizations are combined in a coregistered manner in the final rendering. The coregistration of the secondary image 16.2 and the coordinate system given by the tool positioning can be performed with prior art [7].

Figure 4:
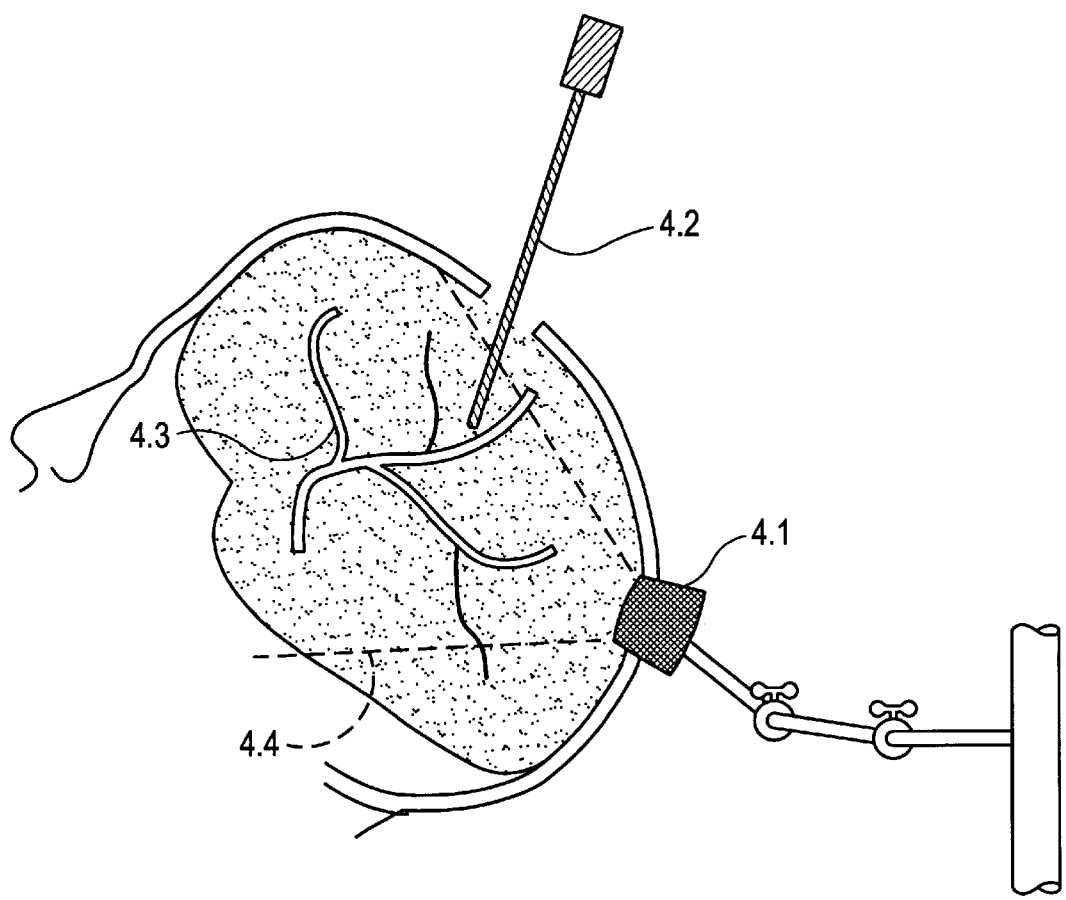
FIG. 4 illustrates how blood vessels can be localized and related to the position of the tool.

Of particular interest during many clinical procedures is the relative position between the tool and neighboring vessels. FIG. 4 illustrates this particular example with a transducer 4.1, a tool 4.2, blood vessels 4.3 located either in 2D or in 3D and the imaged scene 4.4. In fact, any present and future ultrasound modality like tissue imaging, colorflow, power-doppler etc. might be utilized as the basis for the visualizations/graphic presentations described in this invention.

Figure 17:
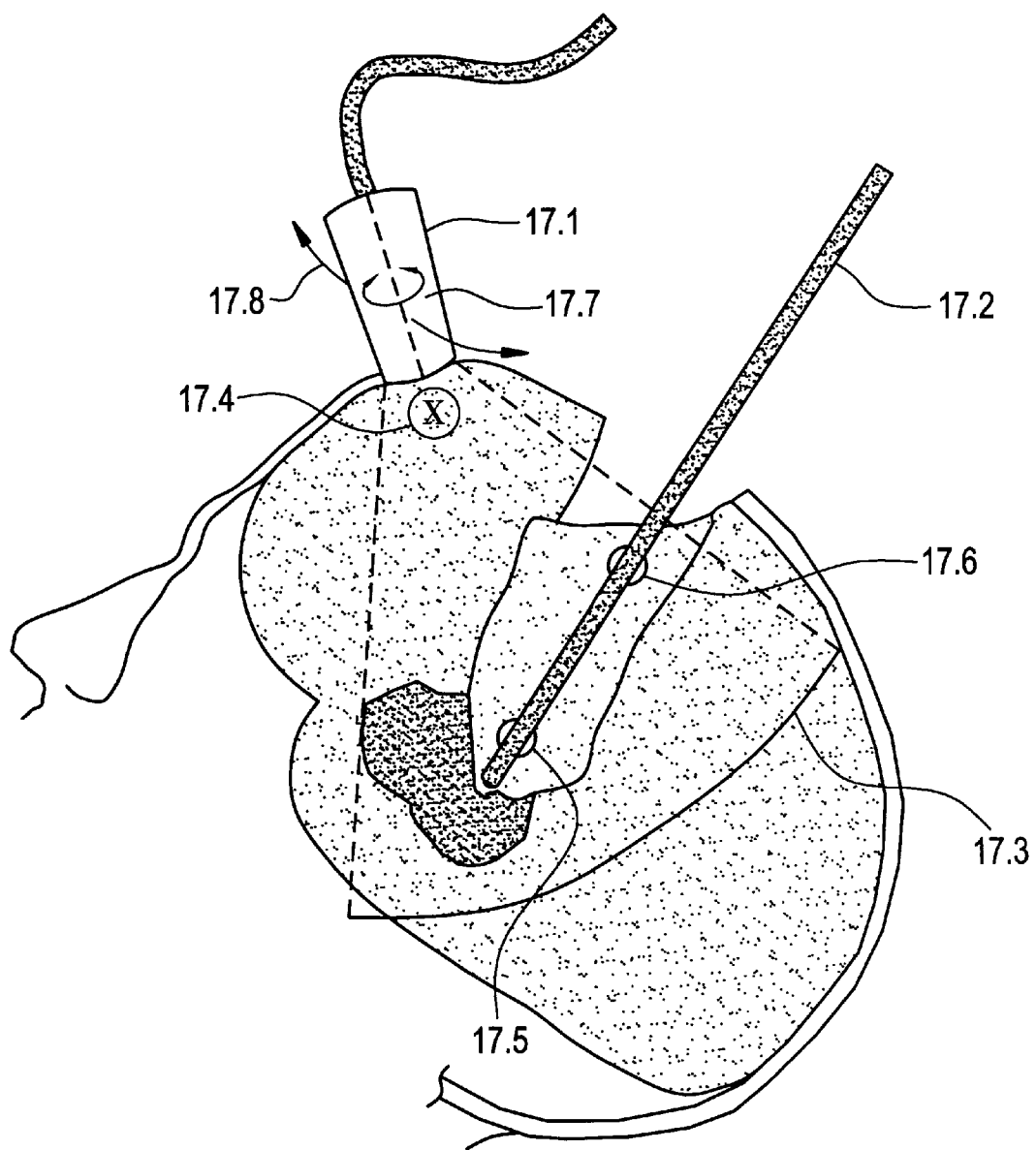
FIG. 17 illustrates how a transducer is moved with rotation and tilting in order to allow for quasi real-time synchronization with the movement of the tool. The 2D scanplane is oriented such that the tool is contained inside the acquired 2D image.

The image resolution of a 2D ultrasonic image directly acquired by a transducer is usually higher than a 2D image extracted from a 3D ultrasonic dataset. The position of the tool can be utilized to modify the orientation of the 2D plane acquired by the transducer. FIG. 17 illustrates this concept. 17.1 is the ultrasound transducer and the tool is given by 17.2. The 2D image acquired by the transducer is given by 17.3. The transducer head (17.4) and two points on a straight tool 17.5 and 17.6 define a unique 2D plane. The transducer is equipped with mechanical orientation devices that can be used to orient the transducer such that the said unique 2D plane is acquired. In this example 17.7 illustrates a rotational motion of the transducer around the center axis and 17.8 indicates a tilting motion for the 2D scanplane. The mechanical orientation devices are controlled according to the position information from the tool such that the operator freely can move the tool and still the 2D ultrasound image acquired by the transducer 17.1 will contain the tool inside the imaged plane. Various time delays between tool movement and transducer readjustment are possible depending on requirements of the said mechanical orientation devices and preferred interactivity for the operator.

Blood vessel detection

The localization of blood vessels is an important task in surgery, especially in endoscopic techniques were the ability to stop bleedings are limited. This section describes a slightly modified version of a method previously described for automatic differentiation of blood signal and tissue signal for the purpose of blood noise reduction in intravascular ultrasound imaging. The method is expected to be more efficient at the high frequencies (high resolution imaging) than on low (overview imaging) frequencies due to increasing scatter from blood versus frequency. A detailed description of the method is provided in [5].

The method to be described here is based on the assumption that the tissue move slower than blood relative to the ultrasound probe. Thus by proper selection of observation interval T, tissue signal will be correlated (if the transit time is longer than T) while blood signal will be uncorrelated (if the transit time is shorter than T). A suitable choice of observation interval is the interval between frames: $T=1/f_r(f_r$ is the frame rate) which typically ranges between 5 ms and 200 ms. This calls for analyzing the signal along the temporal coordinate, i.e. from frame to frame. (The velocity at which blood signal is uncorrelated is about 1 cm/s in intravascular ultrasound imaging at frame rate $f_r$=15 f.p.s.). The cross correlation coefficient is estimated in each spatial point of the image based on the signal from two adjacent frames. The outcome such an estimate ranges between zero and one, values close to one indicating blood while values close to one indicates tissue. From these measurements one can generate a 2D or 3D blood vessel detection map that locates the vascular tree 4.3 in relation to the surgical tool 4.2 or biological structures, see FIG. 4.

Example 2

Description

Figure 2:
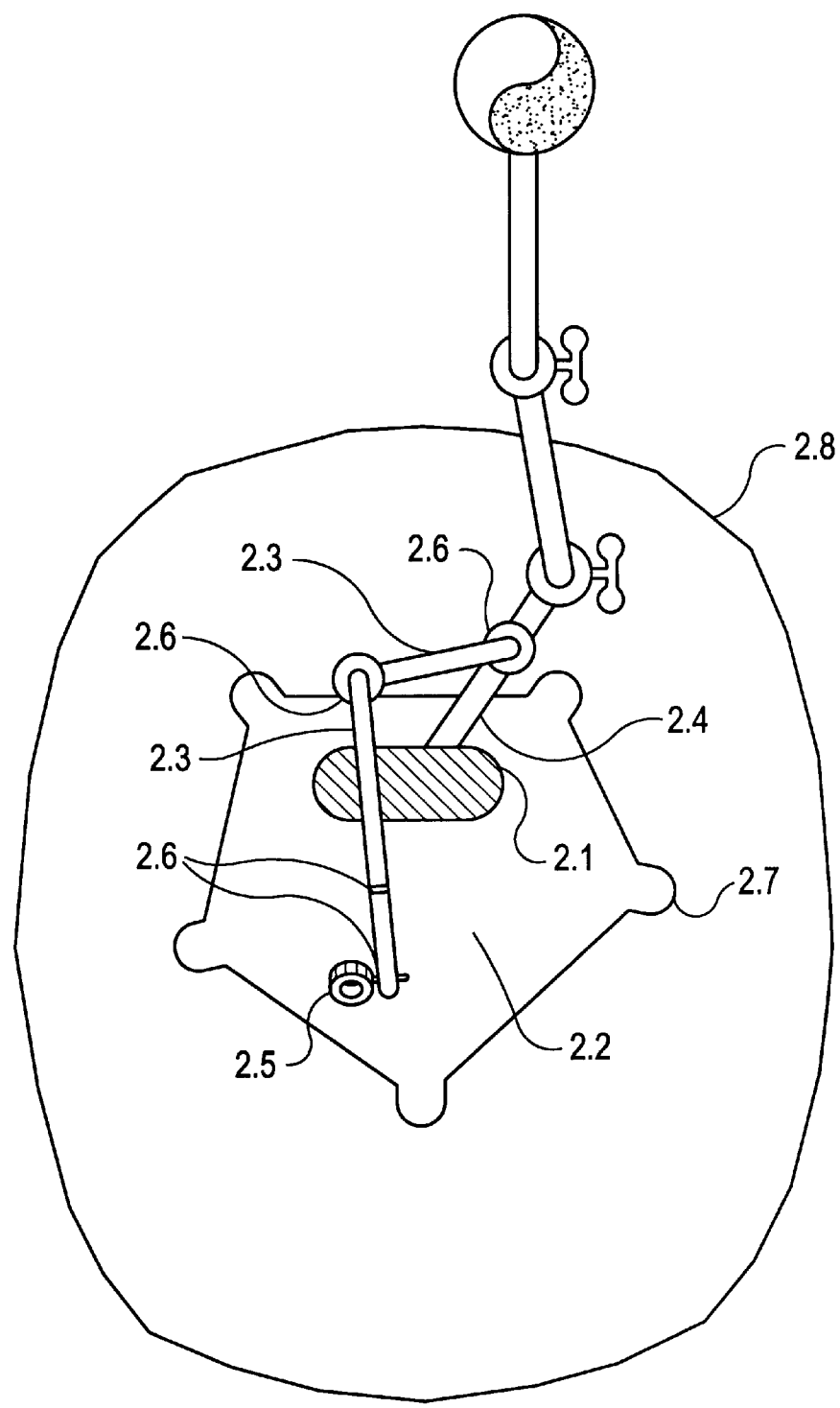
FIG. 2 is a top view illustration of an alternative implementation of that in FIG. 1 except that a mechanical position measuring system is attached to the ultrasound probe arm, making initial calibration obsolete. The tool slides in a guiding tube whose direction is measured and known to the system. Information about the location of the tool tip is provided through direct visualization of the tool in the quasi real-time ultrasound image.

The positioning system for the tool which is described in Example 1 can be replaced with a mechanical system. One option is the six degree-of-freedom articulated arm described by Galloway et al. [2] or the Viewing Wand (ISG Technologies Inc. Ontario, Calif.). However, a five degree-of freedom system may be sufficient for the purpose described here since quasi real-time ultrasound imaging provide information about the location of the tool tip. What is measured is the direction of the tool which requires four angle sensors. A top view of the skull with a five burrhole craniotomy is shown in FIG. 2.

Figure 3:
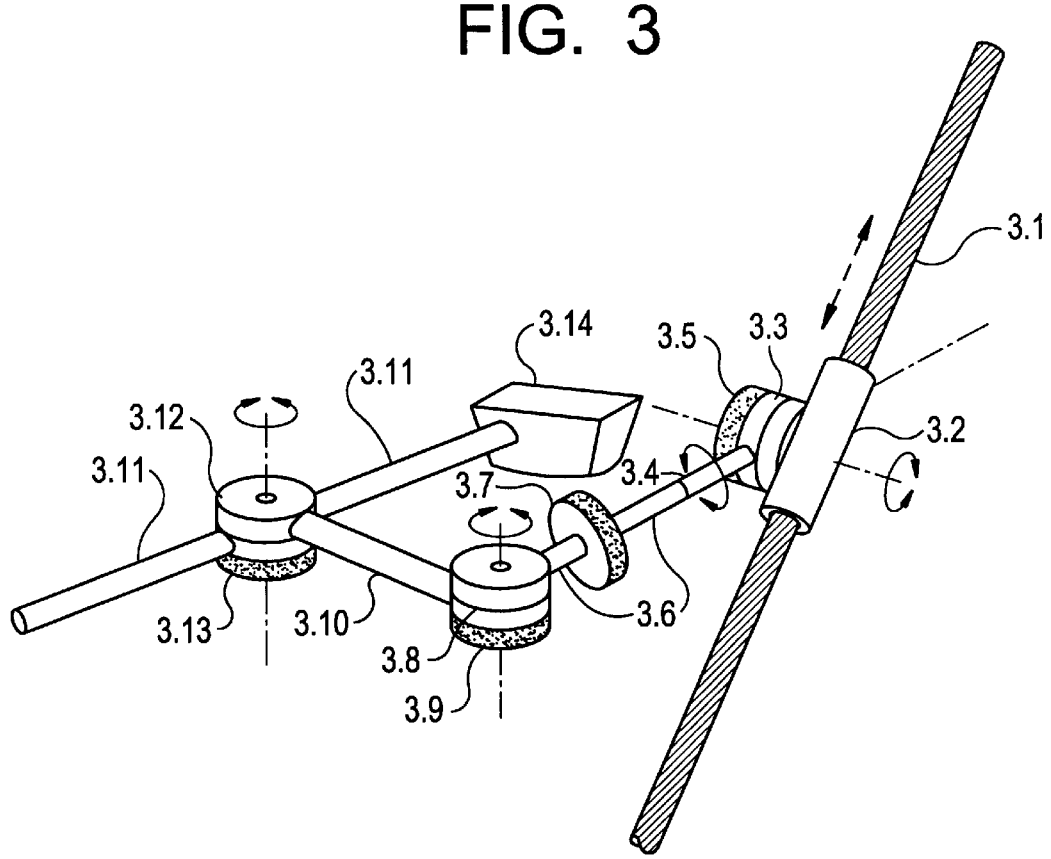
FIG. 3 illustrates is a detailed description of the tool direction measuring system described in FIG. 2. It consists of a guiding tube in which the tool slides and four rotational joints with angle sensors.

The ultrasound probe 2.1 is aligned and fixed on the brain surface 2.2 as described in Example 1. A tool direction measuring device 2.3 is attacthed to the arm 2.4 which holds the ultrasound probe. The surgical tool is entered through a guiding tube 2.5 which is located at the tip of the positioning system. Four rotational axis with angle measurement devices 2.6 allow flexible orientation and direction measurement of the tool relative to the ultrasound probe. A detailed description of the positioning system is provided in FIG. 3. The tool 3.1 is inserted in a guiding tube 3.2. The tool can be slided with low friction in the tube which gives one-degree-of-freedom without position measurement. The guiding tube 3.2 is attached to a rotational joint 3.3 which is located on an arm 3.4. The joint includes an angle measurement device 3.5. The distal arm 3.4 is connected to the proximal arm 3.6 in a way that allows rotation of the distal arm and the guiding tool. The rotational angle is measured by 3.7. A joint 3.8 with an angle measuring device 3.9 connects the proximal outer arm 3.6 and the inner arm 3.10, while the inner arm is attached to the ultrasound probe arm 3.11 by a joint 3.12 with an angle measuring device 3.13. The ultrasound probe 3.14 is fixed to the ultrasound probe arm 3.11.

Case II. Brain Tumor Resection

Example 3

Open Brain Tumor Surgery

Intro

A conventional surgical procedure of a deep sited brain tumor start by resecting an access path through the normal brain tissue which is typically 1–5 cm$^2$ in cross section. Ultrasound imaging, possibly with coregistered MR/CT data as described in Example 1, is supposed to play an role in planning the least damaging route to the tumor in that crossing blood vessels may be discovered (by color flow detection or method described previously). It may also be possible to select an insertion path according to the detection of gyri.

During the resection there is a need for tissue differentiation and global orientation. This can be achieved by the said ultrasound probe which provides overview imaging from the brain surface. Remaining tumor tissue can be localized in the ultrasound image, and the exact location within the brain can be found by moving the tool around within the brain until the tip of the tool appears in the ultrasound image (in the immediate vicinity of the remaining tumor tissue).

There is also a need for high resolution close-up imaging in the resection cavity during resection. Such a probe, the surgeons "second eye", operating in the 10–40 MHz frequency range, may play an important role during resection in order to: i) help in determining the lesion border (in advance) and help the surgeon to decide how much tumor there is left. ii) detect blood vessels in advance in order to pay special attention during resection of the surrounding area. iii) perform quality control after tumor removal, serve as a supplement to or a substitute of the time consuming biopsy sampling which is currently used.

Description

Figure 5:
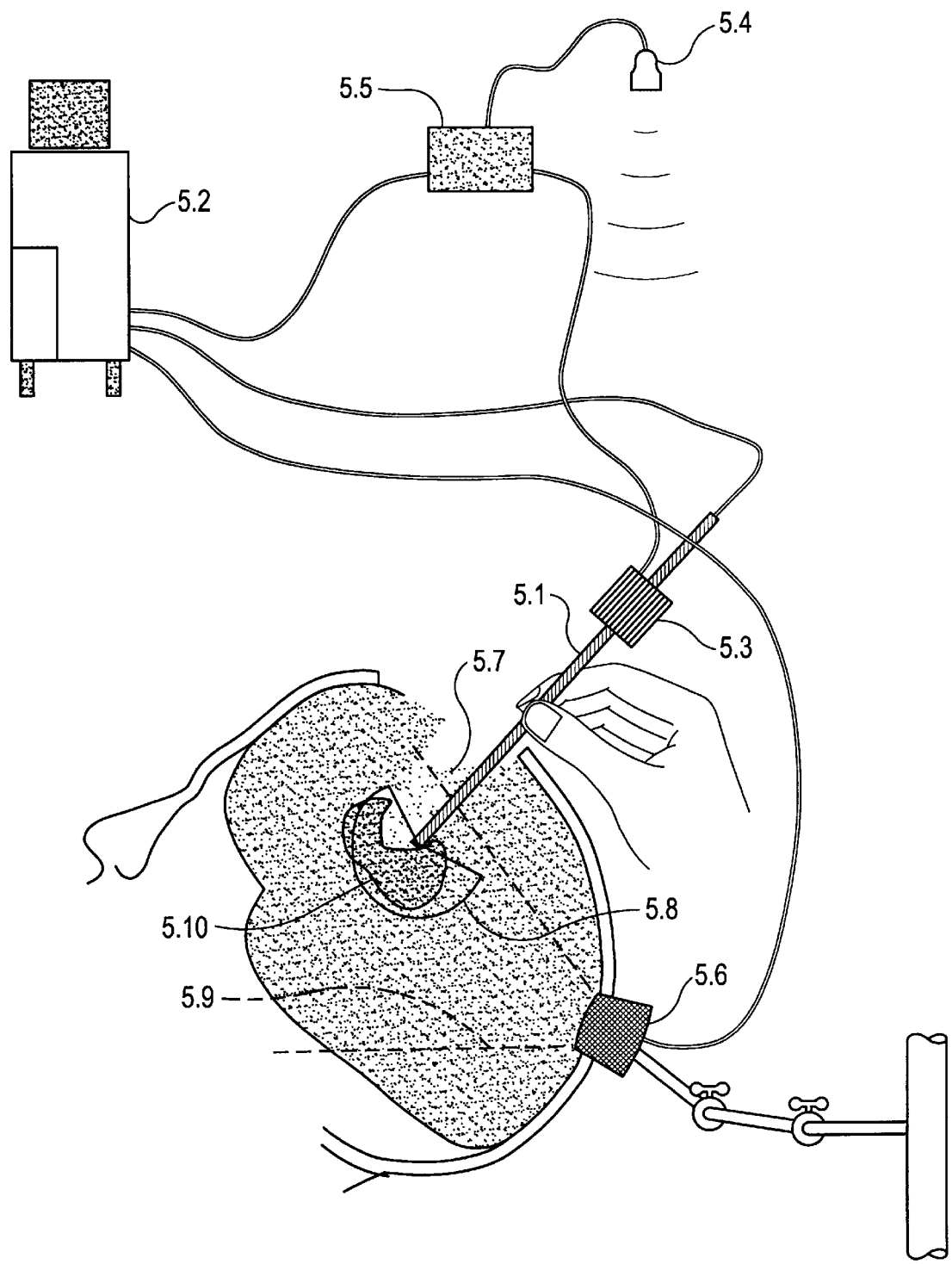
FIG. 5 illustrates the use of a hand-held high-resolution ultrasound probe during brain tumor resection. The position of the probe is measured in order to allow coregistered visualizations of structures including blood vessels, ventricles, lesions and lesion borders. Imaging from a separate burr-hole may be convenient.
Figure 6A:
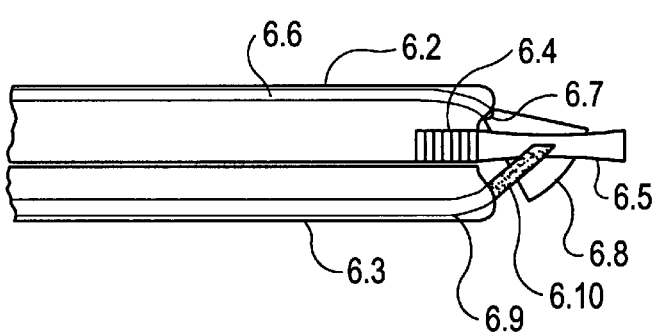
FIG. 6 illustrates one possible realization of an endoscope for brain surgery where (a) provide a top view and (b) a view towards the distal tip of the endoscope. The endoscope consist of two parts: (c) an imaging part which contains an ultrasound probe, and and one or two channels for light source and optical view and (d) a surgical part which contains three channels: one working channel for surgical tools, one channel for suction and one for irrigation.
Figure 6B:
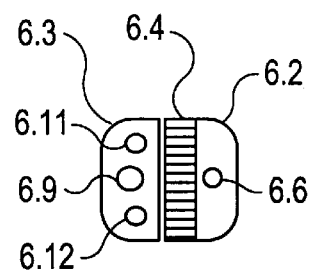
Figure 6C:
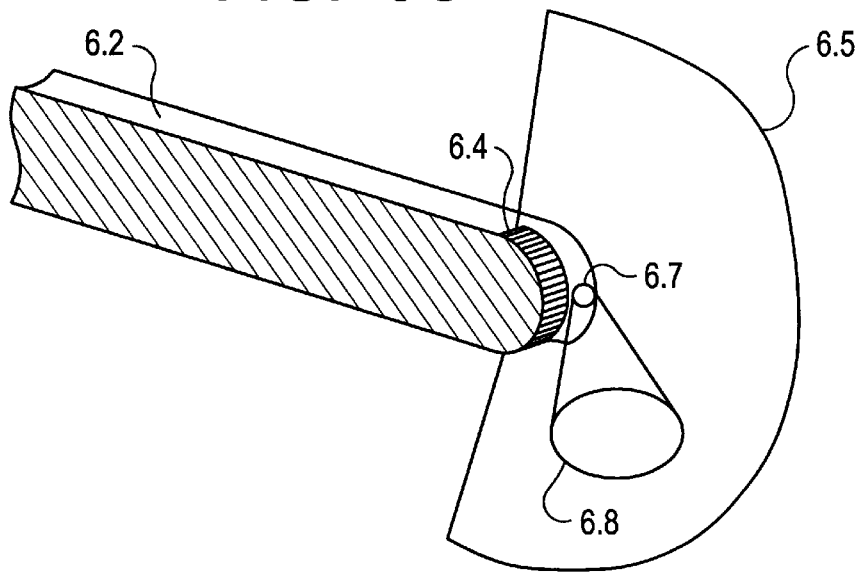
Figure 6D:
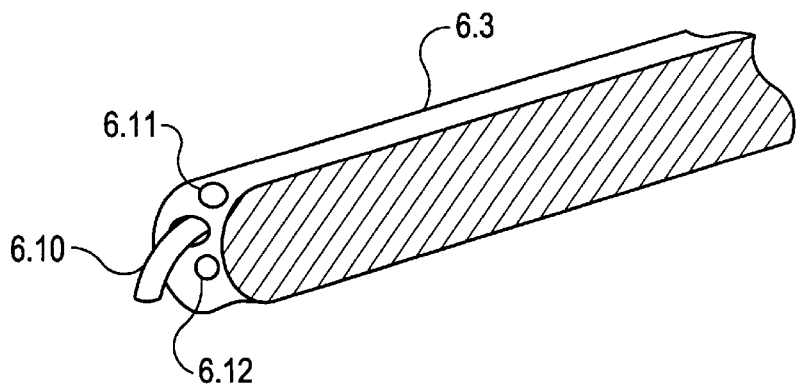
Figure 7A:
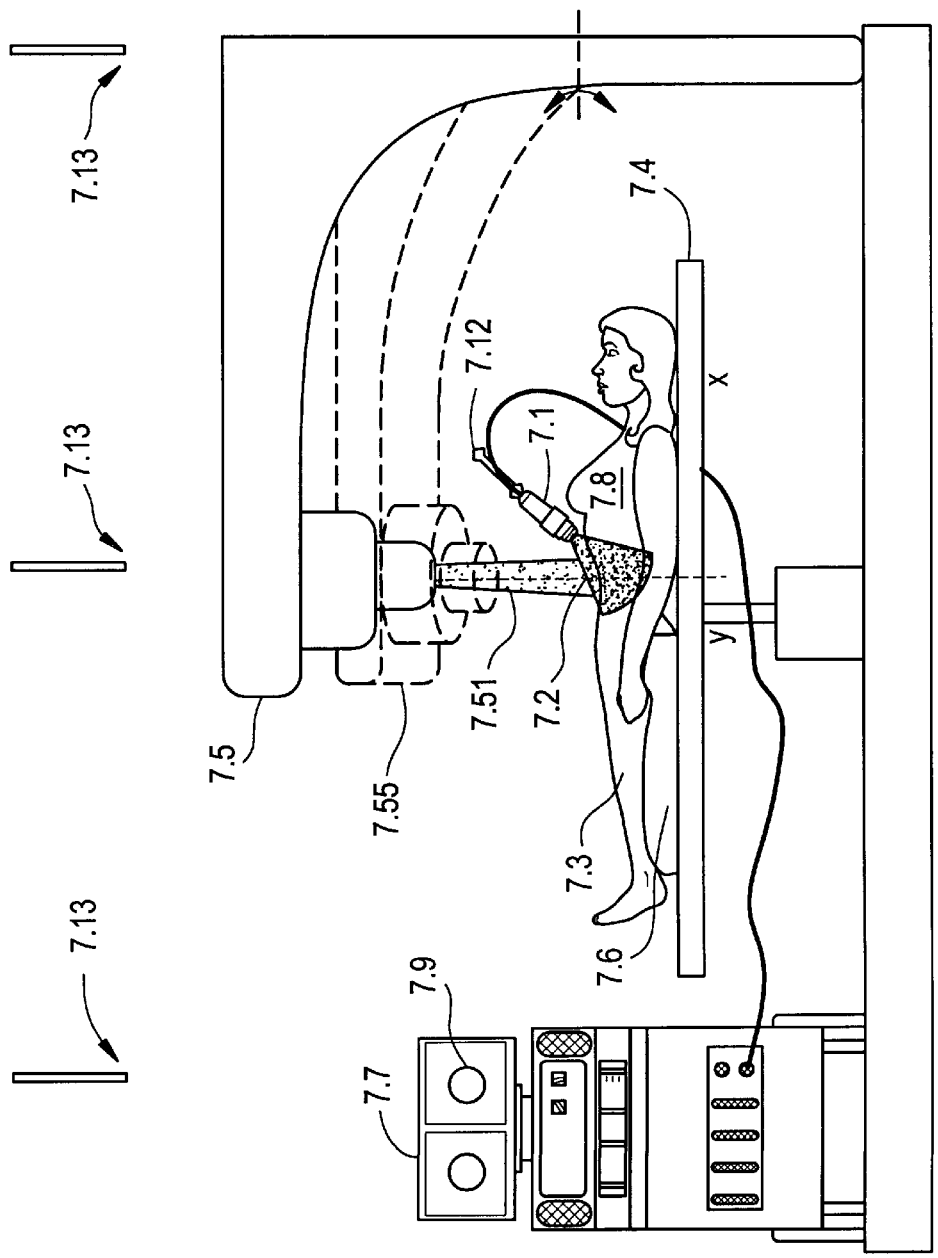
FIGS. 7(a) and (b) are side view (sagittal) and cross sectional (axial) illustrations respectively of ultrasound guided dose planning and/or treatment in radiotherapy. The position and direction of the ultrasound scan plane(s) are measured and coregistered with the radiation field coordinates. This gives the physician opportunity to verify the shape and location of the tumor and/or other biological structures (such as organs or organ parts), and align accurately the radiation field on target.
Figure 7B:
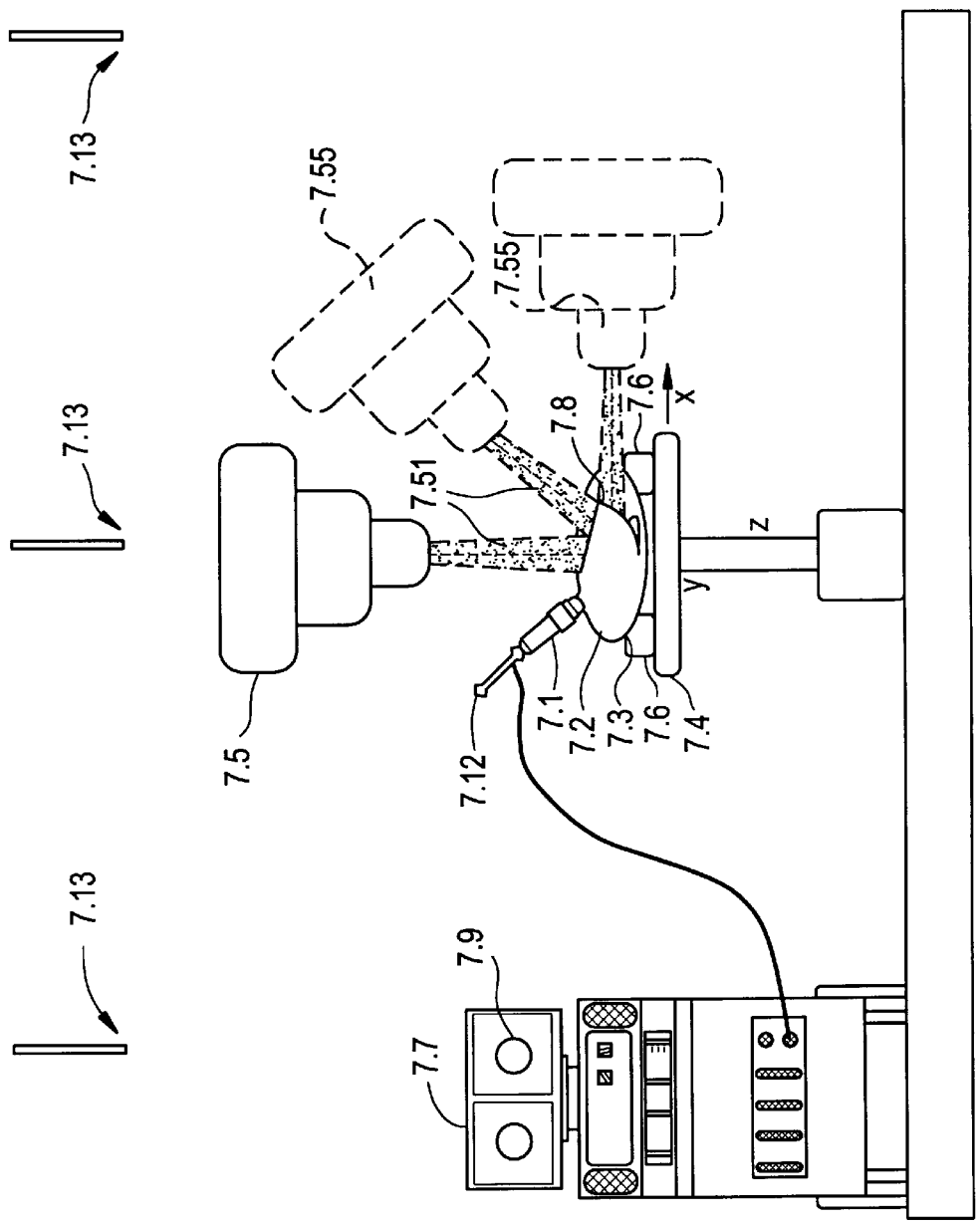
Figure 8A:
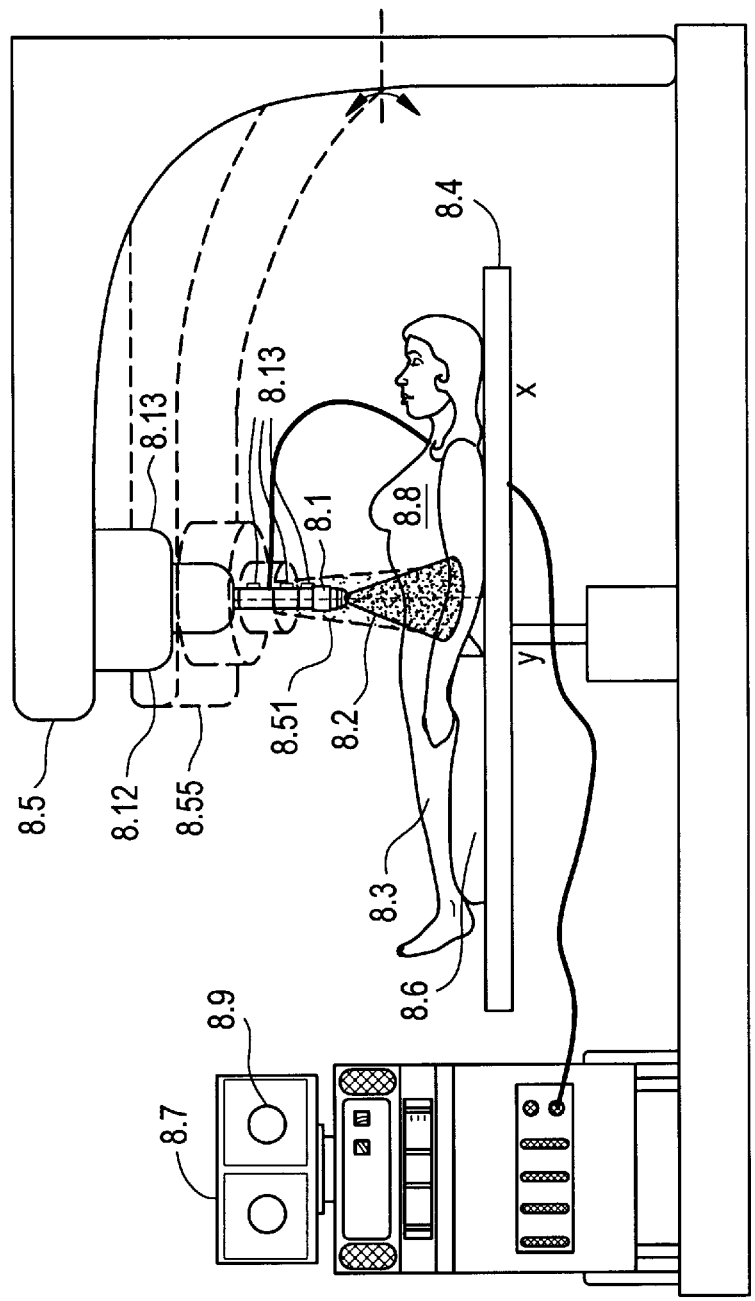
Figure 10A:
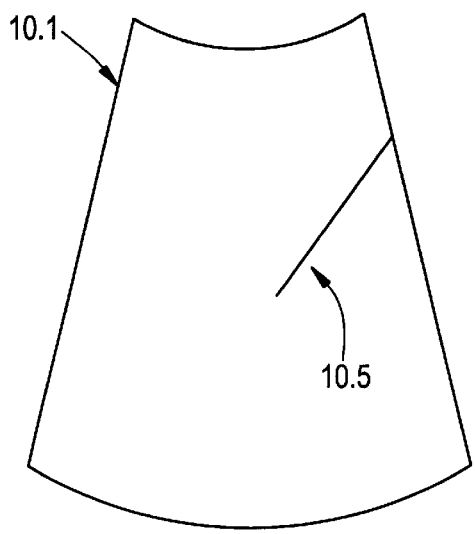
FIG. 10 illustrates how the position of a tool and/or the tool trajectory can be visualized on top of a 2D ultrasonic image.
Figure 10B:
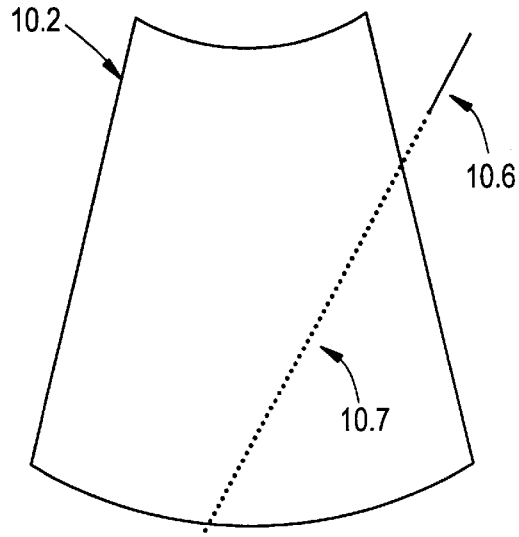
Figure 10C:
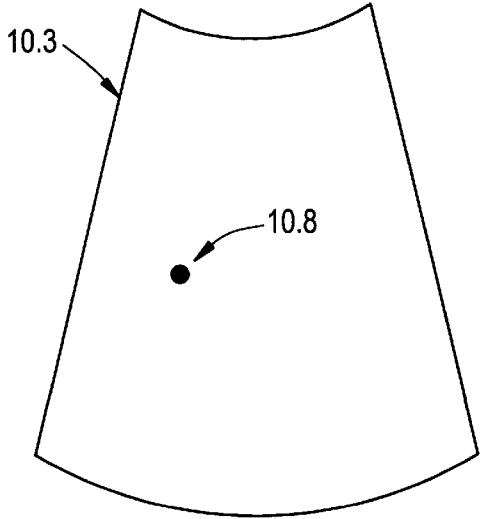
Figure 10D:
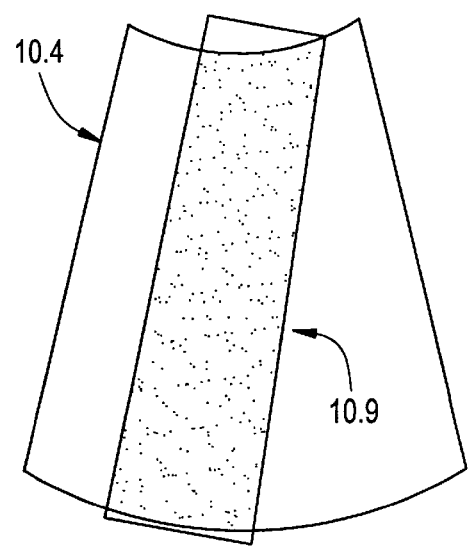
Figure 11A:
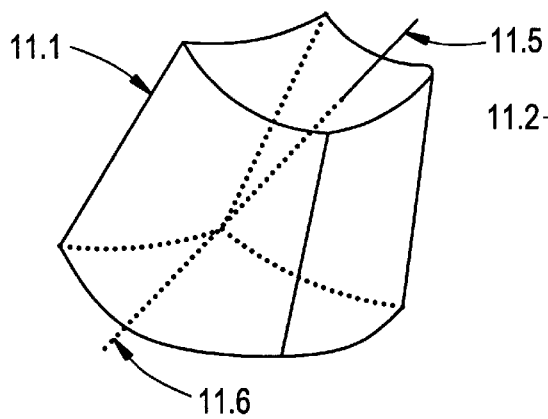
FIG. 11 illustrates how the position of a tool and/or the tool trajectory can be visualized together with either 3D ultrasonic datasets or 2D ultrasonic images extracted from a 3D ultrasonic dataset.
Figure 11B:
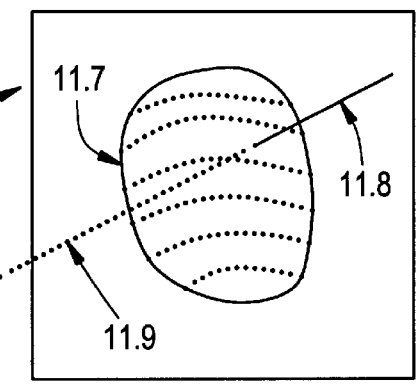
Figure 11C:
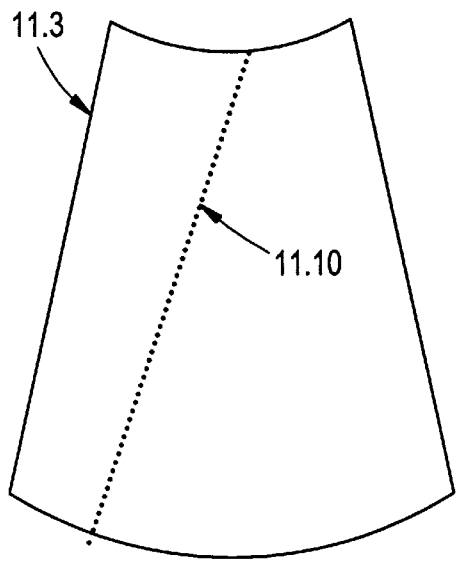
Figure 11D:
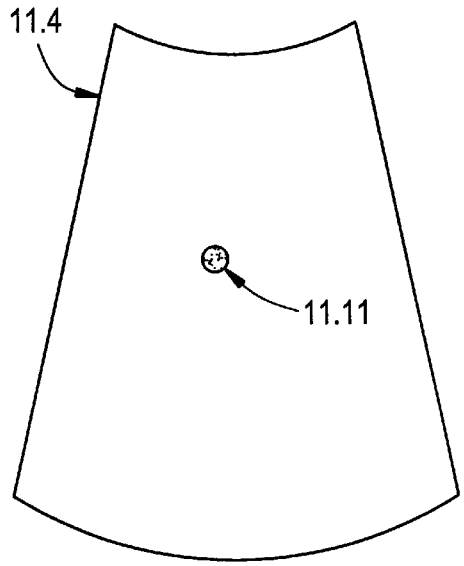
Figure 12A:
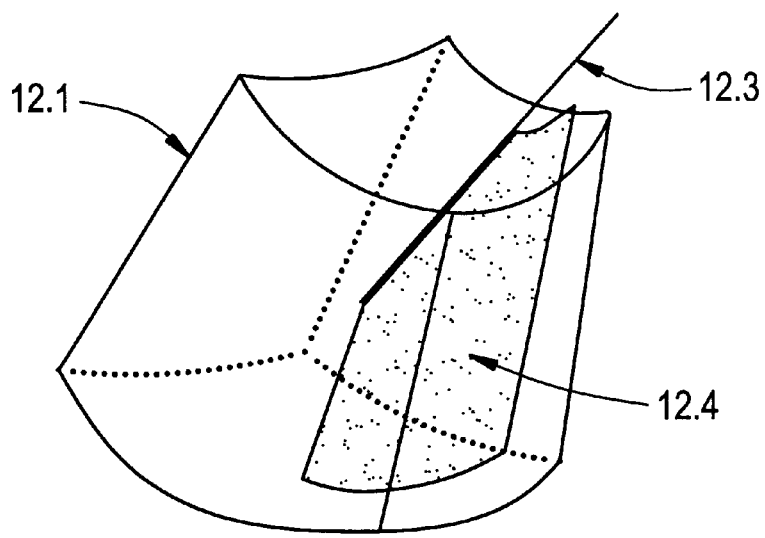
FIG. 12 illustrates how a tool can insert an acoustical shadow in a 2D or 3D ultrasonic dataset.
Figure 12B:
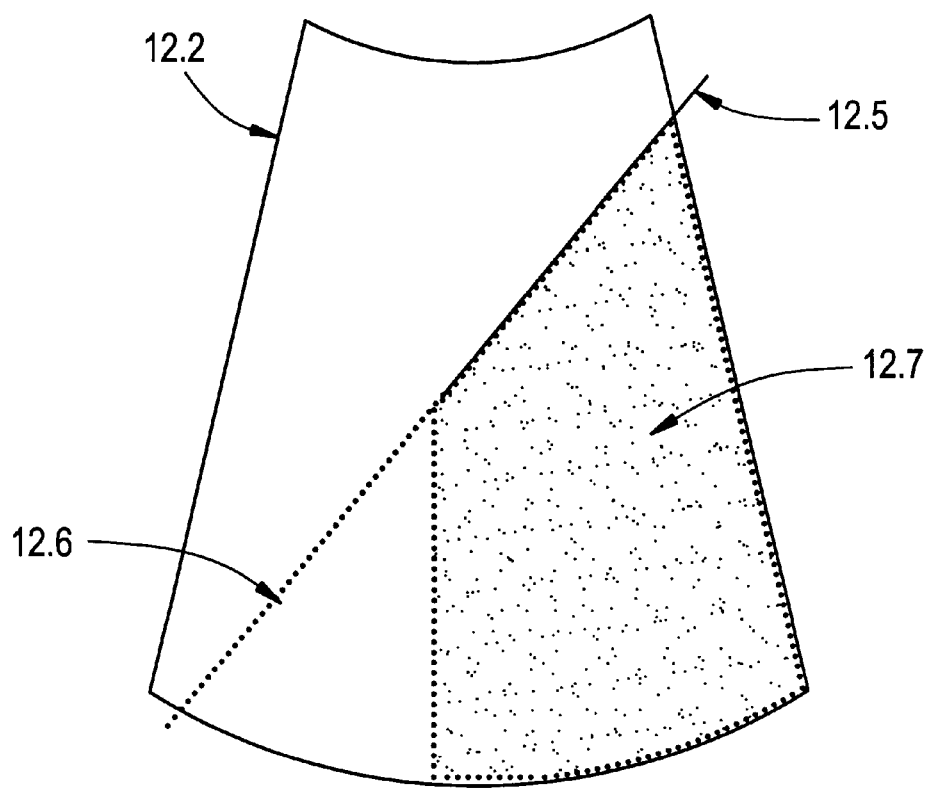
Figure 13A:
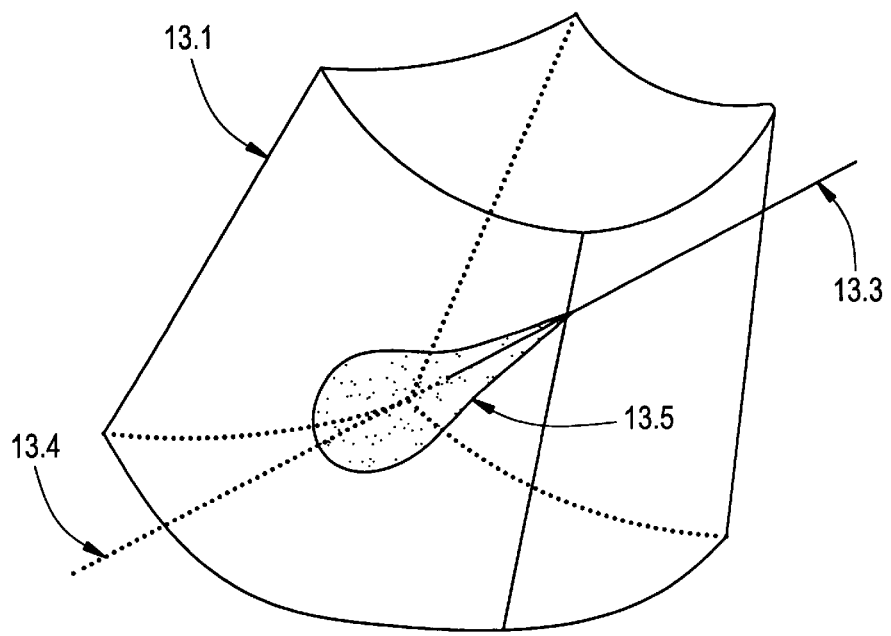
FIG. 13 illustrates how a region of interest or variation in the opacity function can be defined based on the location of the tool and/or tool trajectory in a 3 dimensional ultrasonic dataset.
Figure 13B:
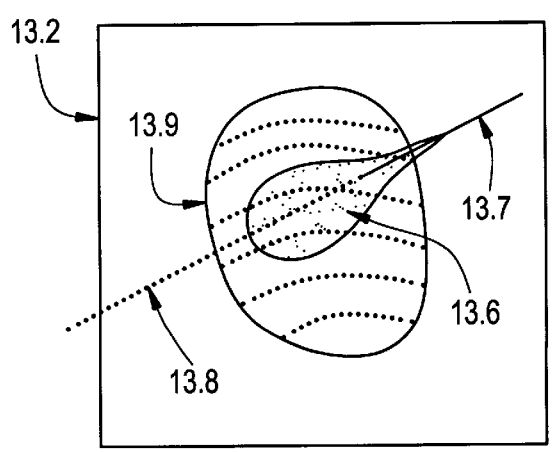
Figure 13C:
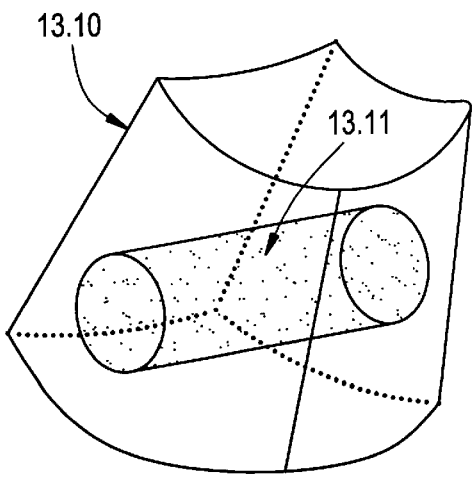
Figure 14A:
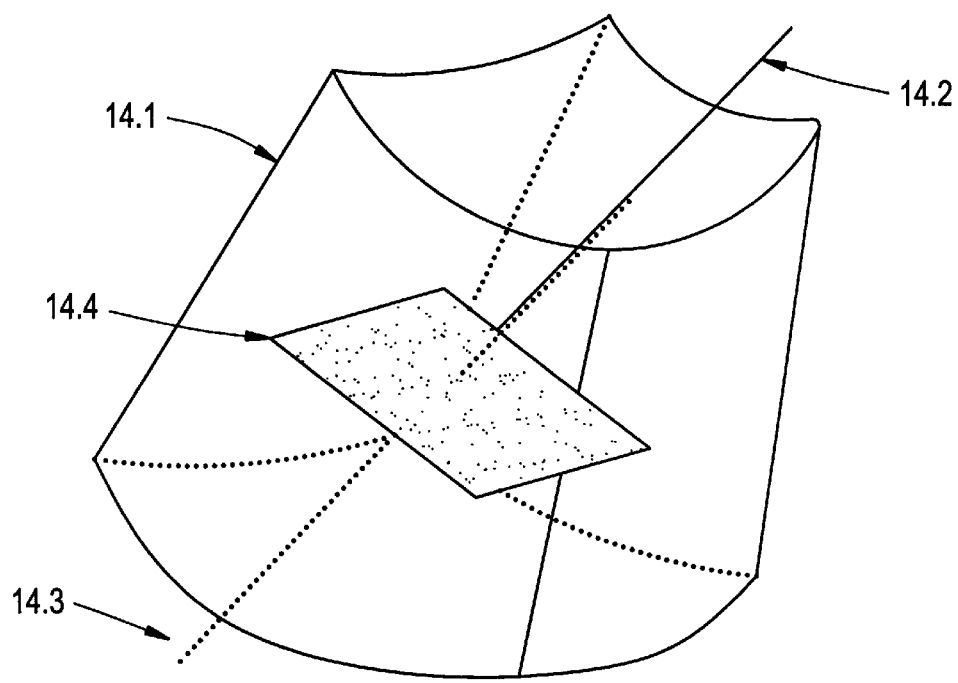
FIG. 14 illustrates how a 2D ultrasonic plane arbitrarily positioned inside a 3D ultrasonic dataset can be defined relative to the position of the tool. Similarly, 3D visualizations can be related in 3D space relative to the position of the tool inside the imaged scene.
Figure 14B:
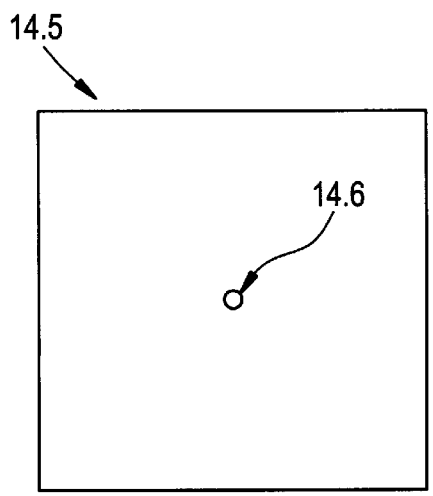
Figure 14C:
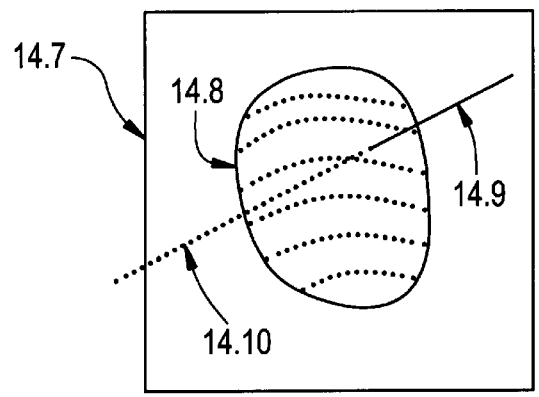
Figure 15A:
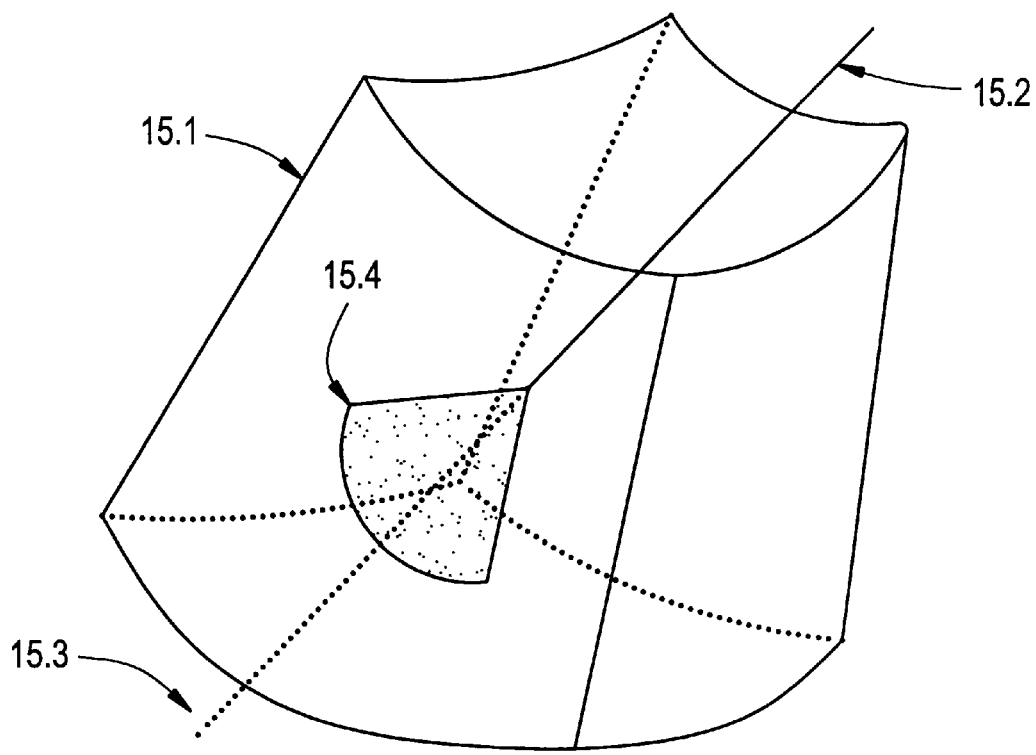
FIG. 15 illustrates how a 2D imaging technique (including high resolution ultrasonic imaging and video imaging) can be combined with a visualization of a 3D ultrasonic image covering the entire region of interest.
Figure 15B:
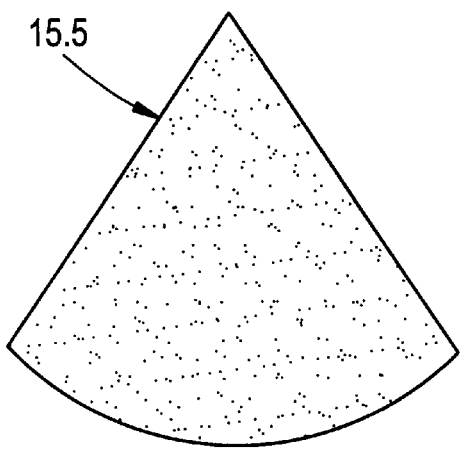
Figure 15C:
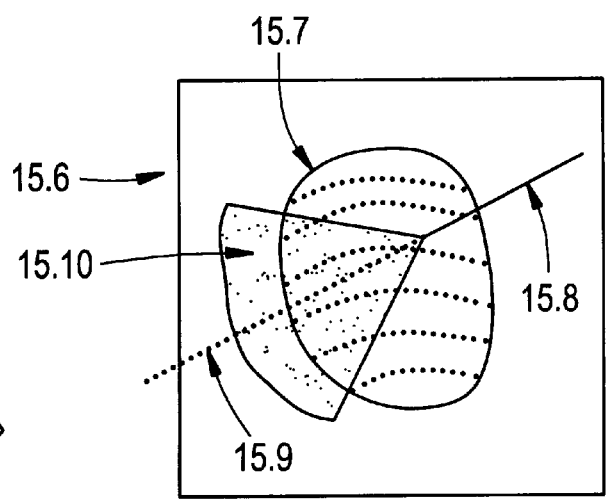

FIG. 5 illustrates a situation where a high frequency, high resolution ultrasound probe is used during brain surgery. This probe 5.1 is connected by a cable to an ultrasound instrument 5.2 which supports dual frequency capabilities. A positioning system measures the position of the high resolution ultrasound probe, here illustrated by the sensor 5.3, the source 5.4 and the control unit 5.5 as described in Example 1. The ultrasound probe 5.6 and the ultrasound instrument 5.2 with a computer is the same as described in Example 1. Acoustic contact between the probe and the tissue is achieved by filling the resection hole with saline 5.7. The tumor 5.10 is partially resected in this illustration. The high frequency ultrasound probe 5.1 is conveniently held by one hand while a surgical tool such as a suction device, diathermy, ultrasound aspirator or a biopsy forceps is held by the other hand. This setting makes it possible to guide the procedure by close-up, quasi real-time high-frequency ultrasound imaging as well as medium frequency (for example 7.5 MHz) overview imaging.

Use

In addition to the above mentioned features, this instrumentation opens up for the following possibilities:

i) Coregistered ultrasound imaging, for example "image in image": The location of the scan plane 5.8 of the high resolution ultrasound probe 5.1 is measured and known to the computer. This scan plane can be extended by data from the 3D ultrasound data set acquired by the probe 5.6. The high resolution short range image 5.8 is inserted in the overlapping part of the lower resolution long range image 5.9. This method "fills in the shadow" of the high resolution ultrasound probe in the lower resolution long range image.

ii) Coregistered MR/CT and high resolution ultrasound imaging: Data from the 3D MR data set may be visualized in a predetermined relation to the location of the scan plane 5.8, for example by visualizing the coinciding MR/CT-image plane.

iii) Visualizations utilizing the localization of the tool can be computed with the techniques as described in Example 1.

iv) The location of the tool can be detected in the overview image by temporal high pass filtering if the tool is continuously moving. This is commonly the case during brain tumor resection. One simple way of doing temporal high pass filtering is to subtract two 2D or 3D data-sets. Stationary targets will cancel while the moving tool will be highlighted. The detected locations might be correlated with a priori knowledge about the tool geometry.

Example 4

Endoscopic Brain Tumor Removal

Intro

The current use of endoscopic techniques for brain tumor removal is limited. Some tumors located close to the ventricular system can be resected by endoscopes that provide optical view in combination with channels for laser and other surgical tools. The primary advantage of endoscopic surgery is a lower risk of damaging normal brain tissue. Endoscopic removal of tumors that are surrounded by normal brain tissue is not possible today due to limitations in imaging techniques, and methods to avoid and stop bleedings are not developed. However, we believe that overview imaging and the integration of high resolution ultrasound imaging at the tip of the endoscope, possibly in combination with signal processing that allows blood vessel detection, may bring this technique a major step forward. The technique described in the following is expected to be useful for removing dense tumors where there is a low risk for bleedings and also patients with bleedings (stroke). If this technique can be developed and be applied through a single burrhole, then treatment can be offered patients who are offered no treatment today.

Description

A suggestion of an endoscope for brain surgery with a high resolution ultrasound imaging capability at the tip is illustrated schematically in FIG. 6. A top view is shown in FIG. 6(*a*) and a front view towards the distal tip is shown in (b). The endoscope 6.1 consists of two parts which can be separated in the imaging part of the endoscope 6.2, see FIG. 6(*c*) and the surgical part of the endoscope 6.3, see FIG. 6(*d*). The ability to separate the endoscope in a fragile imaging part and a more robust surgical part allows different procedures for cleaning and sterilization.

The imaging part of the endoscope 6.1 contains an ultrasound probe at the distal tip. The ultrasound beam can either be generated by a tightly curved switched array 6.4 as illustrated in the figure or by a mechanically driven transducer or by a fixed transducer and a mechanically driven mirror. The ultrasound scan plane 6.5 as illustrated in the figure covers a 180 degrees scan angle providing forward and partially side looking capabilities simultaneously. An optical channel 6.6 can optionally be build into the imaging part of the endoscope. The lens 6.7 is located at the distal tip of the endoscope, and the field of view 6.8 covers the area distal to the tip of the endoscope.

The surgical part of the endoscope 6.3 is less expensive to make and it can be designed in different ways according to the application. The solution suggested in FIG. 6 consists of a channel 6.9 for surgical tools like forceps, suction device 6.10, ultrasound aspirator, diathermy, laser or other. There is also a channel for suction 6.11 and one for irrigation 6.12. The channel 6.9 for surgical tools is shaped so that the surgical tool is forced to cross the ultrasound scan plane in a specified distance from the probe, and the optical field of view 6.8 is also aimed towards this intersection.

Use

The application of an endoscope as described in FIG. 6 will be very equal to the procedure described in Example 3, except that the high resolution ultrasound probe is replaced by the endoscope, and a system for fixating the endoscope in an arbitrary position is required in order to free up the surgeons hands. Ultrasound guidance, prior to and during endoscope insertion is applied as described in Example 3 in order to plan the least damaging route (possibly with coregistered MR/CT data visualization).

The insertion of the endoscope should be guided by the overview ultrasound probe, the high resolution ultrasound probe in the endoscope and by the optical channel. A vessel wall detection capability in the high resolution ultrasound imaging system is desirable since this would reduce the risk of hurting vital blood vessels. The optical vision will be limited or inhibited during endoscope entrances due to the small (or no) cavity in front of the endoscope. However, the endoscope may be re-drawn slightly during the procedure, and saline may be injected under pressure in order to generate a cavity for visual inspection. This requires combined flushing and irrigation in order to clear the sight in case of bleedings.

When the distal tip of the endoscope reaches the tumor surface or bleeding area, resection can start, guided by ultrasound and/or optical vision. The position where the surgical tool crosses the high resolution ultrasound scan plane is known and can be marked on the ultrasound image. This allows positioning of the endoscope to a region where resection is supposed to be done. The surgical tool is then advanced until it is seen in the ultrasound image, and resection can start. A resection cavity is made in front of the endoscope as tumor tissue or blood is removed, and this cavity should be kept open in order to maintain good visual inspection.

This calls for a special system for irrigation and suction which may serve several purposes: i) Provide acoustical contact between the high resolution ultrasound probe and the tissue. ii) Flush and clear the sight for the optical system. iii) Keep the cavity open by applying a pressure that inhibits tissue collapse around the endoscope. iv) Remove the resected tissue and blood from the cavity. There is one irrigation channel in the endoscope, but suction may be performed through both the suction channel and the surgical tool/working channel. This means that a control unit is required which measures the volume flow in all channel and provides a user selectable control of the total flow pattern.

The techniques for coregistered imaging and visualization as described in Example 3 applies here as well during endoscopic tumor resection.

Case III. Radiotherapy

One of the real challenging tasks during radiotherapy of cancer is positioning of patients in the radiation field. The patient is placed in a radiation simulator after a diagnostic survey and tumor/organ mapping using MR, CT, X-ray or ultrasound imaging. This machine is functionally a copy of the radiotherapy machine with the same characteristics regarding patient positioning and radiation field characteristics, but where the high energy radiation field is replaced by low energy X-ray. In the simulator, the physician will plan the actual treatment by applying low energy X-ray fields and simultaneously record the X-ray images. These images are now a map or a control of the correct targeting of the tumor/organs by the radiation fields, and are used to ensure that the surrounding tissues (often critical organs) does not receive a lethal dose of high energy radiation. The patient is aligned in the simulator machine with customized braces and patient holders, preventing the patient from moving on the couch. Ink marks are applied to the skin of the patient according to alignment lasers calibrated to transfer the patient from the coordinate system of the simulator machine to the coordinate system of the therapeutic machine.

The patient then is transferred to the therapeutic high radiation machine and aligned on the couch with the same braces and supports used in the simulator and according to the alignment lasers. Low energy X-ray images are often taken with the therapeutic machine (minimal dose shots) to verify the patient alignment according the simulator X-ray images.

Using ultrasound 2D or 3D imaging as an aid for locating the target area and positioning the patient in the simulator and in the therapeutic machines will increase the probability of actually radiating the targeted area, correcting for movements of the skin and internal organs and speed up alignment of the patient. This is especially true in cases where the tumor is not visible on conventional X-ray images.

Example 5

Ultrasound guided location of tumors and target areas requires accurate knowledge of the transducer position and the image orientation relative to the coordinate system of the simulator or therapeutic machine. This example describes a possible design of a system for ultrasound guided target verification and patient alignment in a high energy radiation therapeutic machine.

An ultrasound probe (7.1) has attached a position and directional device (7.12), being a part of a fixed traction detection system (7.13) (previously described), keeping track of the absolute coordinates of the ultrasound image (7.2) relative to the coordinate system of the simulator (7.5). The patient (7.3) is placed on the simulator couch (7.4), having three-degrees-of-freedom movement (x-y-z-positioning), and stabilized with customized braces and supports (7.6). The target area (7.8) (tumor/organ) is scanned by 2D or 3D ultrasound imaging (7.7) and the physician marks or traces the radiation target (7.8) (tumor) on the ultrasound image (7.9). The coordinates of the targeted area, calculated by the traction detection system (7.13) is transferred to the coordinate system of the simulator (7.5) and the radiation fields are positioned to intersect the target area (7.8) accordingly. During the procedure of positioning the simulator fields (7.51) relative to the ultrasound image coordinates, the direction and extent of these fields (7.51) can be projected onto the ultrasound image (7.9). The quasi-real-time feedback of radiation field positioning (7.55) gives the physician opportunity to make on-the-fly adjustments and corrections to the treatment scheme, reducing the time spent in the simulator due to fewer exposure and development cycles with conventional X-ray imaging.

As the planning of the radiation therapy is finished the patient is transferred to the therapeutic high radiation machine, aligned and positioned according to the treatment scheme and simulator data. By having installed a similar ultrasound system at the therapeutic machine as at the simulator, 2D or 3D ultrasound imaging can again be utilized to correctly position and align the patient and the high energy radiation field. Also the position detection system at the therapeutic machine allows last minute correction for field adjustments due to skin and internal organ movement.

Example 6

This is a simplified version of the previous example. It reduces investment costs at the expense of freedom of operability but includes the main features.

An ultrasound probe (8.1) is rigidly connected to the simulator (8.5) with a two-degree-of freedom arm (8.12) supporting movement of the ultrasound transducer (8.1) in the plane spanned by the ultrasound image sector (8.2) aligned with the radiation field center (8.51). The arm joints (8.13) are supplied with angle sensors. These sensors, in combination, measures the position and orientation of the ultrasound transducer (8.1) relative to the coordinate system of the simulator (8.5). The patient (8.3) is placed on the simulator couch (8.4), having three degrees of freedom movement (x-y-z-positioning), and stabilized with customized braces and supports (8.6). Scanning the target area (8.8) (tumor) by 2D or 3D ultrasound imaging (8.7) the direction of the radiation field (8.51) can be projected onto the ultrasound image (8.9). The physician marks the desired point for the radiation field center in the ultrasound image (8.9), the coordinates of this point are transferred to the coordinate system of the simulator (8.5) and the direct feedback of target position will aid the placement of radiation fields (8.51) and their relative angles (8.55) to the patient (8.3).

By installing a similar ultrasound system (8.1, 8.2, 8.7) at the therapeutic machine, 2D or 3D ultrasound imaging can be applied to correctly position and align the patient and the high energy radiation field. Also the position detection system at the therapeutic machine allows last minute correction for field adjustments due to skin and internal organ movement.

Ultrasound imaging combined with position feedback linked to therapeutic radiation system gives an advantage of reducing simulator time, increasing patient safety, minimizing high energy radiation exposure to sensitive organs and increasing treatment quality control during radiation therapy.

SUMMARY OF THE INVENTION

It is a general object of the present invention to provide feedback information to the operator during a clinical procedure that helps to locate and orient tools in relation to biological structures that is not visible to the human eye. At least one ultrasound imaging system is included to generate image information about the biological structures, however, other imaging systems can optionally be included in addition (including ultrasound). The method applies to both 2D and 3D ultrasound imaging.

The given definition of the term tool is very broad which means that this method finds applications within different clinical fields including invasive surgery, non-invasive therapy and diagnostics. Possible tools are simple mechanical devices used in surgery, more complex multifunction devices like endoscopes, energy fields in radiotherapy or laser-light in diagnostic equipment.

The invention allows for arbitrary movement of the tool relative to the imaging devices including freehand movement of the tool or ultrasound probe.

The localization of the tool in relation to an ultrasound image allows computation of various visualizations that may be synchronized with the operators tool movement. One example is visualisation of multiplane images that intersects the axis of the tool in order to visualize structures that is is located in vicinity of the tool and distal to its tip. Another example is to apply image processing functions that limit the amount of data that is fed to the display in order to focus on a special area, for example by applying an opacity function to a 3D data set. Techniques like image-in-image is possible if more than one ultrasound imaging system is in use.

References

[1] P. J. Kelly, "Stereotactic imaging, surgical planning and computer-assisted resection of intracranial lesions: methods and results.", *Advances and technical standards in neurosurgery*, vol. 17, pp. 77–118, 1990.

[2] R. L. Galloway and R. J. E. Maciunas C.A., "Interactive Image-Guided Neurosurgery", *IEEE Trans. Biomed. Eng.*, vol. 39, NO. 12, pp. 1226–1231, 1992.

[3] P. Kumar, et al., "Evaluation of Intraoperative Ultrasound in Neurosurgery", *Annals Academy of Medicine*, vol. 22 No.3 (Suppl), pp. 422–27, 1993.

[4] J. C. Sutcliffe and R. D. E. Battersby, "Intraoperative ultrasound-guided biopsy of intracranial lesions: comparison with free hand biosy", *British Journal of Neurosurgery*, vol. 5, pp. 163–168, 1991.

[5] A. Gronningsaeter, "Reduction of acoustic and electronic noise in intravascular ultrasound imaging", Dr. ing. thesis, Norwegian Institute of Technology, Trondheim Norway, 1992.

[6] D. G. T. Thomas and N. D. Kitchen, "Minimally invasive surgery. Neurosurgery.", *BMJ*, vol. 308, pp. 126–128, 1994.

[7] "Probe-correlated viewing of anatomical image data". Patent application, PCT/CA90/00404, filing date: Nov. 21, 1990.

We claim:

1. A method for generating quasi real-time feedback information about tissue characteristics and the position of anatomical objects relative to at least one tool used during clinical procedures in living biological structures, employing an ultrasound transducer and comprising:

acquiring at least one 2D and/or 3D ultrasonic image of anatomical objects in a living biological structure during a clinical procedure, freely moving said at least one tool and/or said ultrasound transducer, localizing said at least one tool and/or tool trajectory thereof in an imaged scene covered by said ultrasonic image, computing visualizations of the imaged scene by utilizing the geometric localizations of said at least one tool in the processing and/or visualization of said ultrasonic images, and displaying the resulting visualizations on a display unit in order to provide quasi real-time feedback to the operator.

2. Method according to claim 1, wherein said localization is utilized to adjust the acquisition to optimize the resolution of the image in certain regions of a 3D data set.

3. Method according to claim 1, wherein said localization is utilized to adjust the acquisition such that the orientation of a 2D scan plane changes with movement of said at least one tool.

4. Method according to claim 1, wherein said localization is utilized to process said ultrasonic images in order to compensate for artifacts like shadowing effects caused by said at least one tool and/or modify the signature caused in the ultrasonic images by the at least one tool itself.

5. Method according to claim 4, wherein the artifacts are detected by a geometric computation utilizing information about profiles of an emitted ultrasonic beam (the point-spread function), and tool position to determine the spatial locations that might be affected by the at least one tool.

6. Method according to claim 4, wherein the artifacts are removed by substituting image data from a prior acquiring step.

7. Method according to claim 4, wherein the artifacts are made transparent in said visualizations.

8. Method according to claim 1, wherein said ultrasonic images include a 3D ultrasonic image that is visualized by assigning an opacity function which depends on said localization of said at least one tool and/or tool trajectory thereof.

9. Method according to claim 8, wherein said opacity function is computed by preselecting a spatial neighborhood relative to the localization of said at least one tool and/or tool trajectory thereof and increasing the transparency of values outside this neighborhood in the visualization of the 3D scene, and wherein the resulting visualization emphasizes ultrasonic measurements in the vicinity of said at least one tool and/or tool trajectory thereof.

10. Method according to claim 1, wherein said ultrasonic images include a 3D ultrasonic image that is visualized by extracting at least one 2D plane from a 3D dataset such that the position of the 2D plane is related to the localization of said at least one tool and/or tool trajectory thereof.

11. Method according to claim 10, wherein said 2D plane is related to the at least one tool direction or tool trajectory thereof by using said direction as a normal to a set of parallel 2D planes or as a rotation axis for a set of rotated 2D planes.

12. Method according to claim 11, wherein the 2D plane is used as a starting point for a raytracing process creating a 3D visualization perpendicular to the 2D plane.

13. Method according to claim 11, wherein said visualization of a 3D ultrasonic dataset is viewed from a direction that is fixed relative to the position and direction of the at least one tool.

14. Method according to claim 1, wherein said acquisition of a 2D ultrasonic image is performed in a way that ensures a longitudinal cross sectional image of said too during movement of said at least one tool.

15. Method according to claim 14, wherein said acquisition of a 2D ultrasonic image is performed by tilting and/or rotating the 2D plane by a mechanical motion.

16. Method according to claim 1, wherein said 3D acquisition is realized by a tilting movement of a 2D scan lane, and the resolution is optimized in a narrow sector which surrounds said at least one tool and follows the movement of said at least one tool.

17. A method for generating quasi real-time feedback information about tissue characteristics and the position of anatomical objects relative to at least one tool used during clinical procedures in living biological structures, employing an ultrasound transducer and comprising:

acquiring at least one 2D and/or 3D ultrasonic image of anatomical objects in a living biological structure during a clinical procedure, freely moving said at least one tool and/or said ultrasound transducer, controlling ultrasonic viewing scan plane selection by the position and orientation of the at least one tool so as to retain viewing of the at least one tool superimposed into the scan plane while the at least one tool is moved relative to the ultrasound transducer, localizing said at least one tool and/or tool trajectory thereof in an imaged scene covered by said ultrasonic image, computing visualizations of the imaged scene by utilizing the geometric localizations of said at least one tool in the processing and/or visualization of said ultrasonic images, and displaying the resulting visualizations on a display unit in order to provide quasi real-time feedback to the operator.

18. Apparatus for generating quasi real-time feedback information about tissue characteristics and the position of anatomical objects relative to at least one tool used during clinical procedures in living biological structures, employing an ultrasound transducer and comprising:

means for acquiring at least one 2D and/or 3D ultrasonic image of anatomical objects in a living biological structure during a clinical procedure, means for freely moving said at least one tool and/or ultrasound transducer, means for localizing said at least one tool and/or tool trajectory thereof in an imaged scene covered by said ultrasonic image, means for computing visualizations of the imaged scene by utilizing the geometric localizations of said at least one tool in the processing and/or visualization of said ultrasonic images, and means for displaying the resulting visualizations on a display unit in order to provide quasi real-time feedback to the operator.

* * * * *